(12) United States Patent
Jankowski

(10) Patent No.: US 8,393,513 B2
(45) Date of Patent: Mar. 12, 2013

(54) SURGICAL STAPLING APPARATUS INCLUDING AN ANVIL AND CARTRIDGE EACH HAVING COOPERATING MATING SURFACES

(75) Inventor: Bruce K. Jankowski, North Attleboro, MA (US)

(73) Assignee: Covidien LP, Mansfield, MA (US)

( * ) Notice: Subject to any disclaimer, the term of this patent is extended or adjusted under 35 U.S.C. 154(b) by 444 days.

(21) Appl. No.: 12/008,298

(22) Filed: Jan. 9, 2008

(65) Prior Publication Data

US 2008/0110960 A1  May 15, 2008

Related U.S. Application Data

(63) Continuation of application No. 11/113,928, filed on Apr. 25, 2005, which is a continuation of application No. 10/411,686, filed on Apr. 11, 2003, now Pat. No. 7,070,083.

(60) Provisional application No. 60/372,356, filed on Apr. 11, 2002.

(51) Int. Cl.
A61B 17/068 (2006.01)
(52) U.S. Cl. .................. 227/176.1; 227/175.1
(58) Field of Classification Search ............ 227/175.1, 227/176.1, 180.1; 606/28, 135
See application file for complete search history.

(56) References Cited

U.S. PATENT DOCUMENTS

| | | | |
|---|---|---|---|
| 3,771,526 A | 11/1973 | Rudle | |
| 3,822,818 A | 7/1974 | Strekopytov et al. | |
| 4,957,499 A * | 9/1990 | Lipatov et al. | 606/153 |
| 5,205,459 A | 4/1993 | Brinkerhoff et al. | |
| 5,263,629 A | 11/1993 | Trumbull et al. | |
| 5,282,810 A * | 2/1994 | Allen et al. | 606/150 |
| 5,368,599 A | 11/1994 | Hirsch et al. | |
| 5,452,837 A | 9/1995 | Williamson, IV et al. | |
| 5,582,611 A * | 12/1996 | Tsuruta et al. | 606/46 |
| 5,653,373 A | 8/1997 | Green et al. | |
| 5,697,542 A | 12/1997 | Knodel et al. | |
| 5,709,680 A | 1/1998 | Yates et al. | |
| 5,769,303 A | 6/1998 | Knodel et al. | |
| 5,779,131 A | 7/1998 | Knodel et al. | |
| 5,779,132 A | 7/1998 | Knodel et al. | |
| 5,865,361 A | 2/1999 | Milliman et al. | |
| 5,871,135 A * | 2/1999 | Williamson, IV et al. | 227/178.1 |
| 5,876,401 A | 3/1999 | Schulze et al. | |
| 5,915,616 A | 6/1999 | Viola et al. | |
| 5,964,394 A | 10/1999 | Robertson | |
| 6,032,849 A | 3/2000 | Mastri et al. | |
| 6,045,560 A | 4/2000 | McKean et al. | |
| 6,096,037 A * | 8/2000 | Mulier et al. | 606/49 |
| 6,241,139 B1 | 6/2001 | Milliman et al. | |
| 6,330,956 B1 | 12/2001 | Willinger | |
| 6,503,259 B2 | 1/2003 | Huxel et al. | |
| 6,736,813 B2 | 5/2004 | Yamauchi et al. | |
| 7,179,267 B2 * | 2/2007 | Nolan et al. | 606/153 |
| 2003/0009193 A1 | 1/2003 | Corsaro | |
| 2003/0114851 A1 | 6/2003 | Truckai et al. | |
| 2004/0082963 A1 * | 4/2004 | Gannoe et al. | 606/153 |

FOREIGN PATENT DOCUMENTS

| | | |
|---|---|---|
| EP | 0878169 | 11/1998 |
| EP | 1090592 | 4/2001 |
| EP | 1254636 | 11/2002 |
| WO | WO 01/54594 | 8/2001 |

* cited by examiner

*Primary Examiner* — M. Alexandra Elve
*Assistant Examiner* — Nathaniel Chukwurah

(57) ABSTRACT

Surgical stapling apparatus are disclosed including an anvil having a working surface with a shaped topography, and a staple cartridge, in juxtaposition with the anvil. The staple cartridge includes a working surface with shaped topography which is complementary to the shaped topography of the working surface of the shaped anvil. When the anvil and the staple cartridge are approximated with or toward one another, at least a portion of the working surface of the anvil cooperates with at least a portion of the working surface of the staple cartridge to enhance alignment of the staple cartridge and the anvil in at least one of a transverse and longitudinal direction.

14 Claims, 16 Drawing Sheets

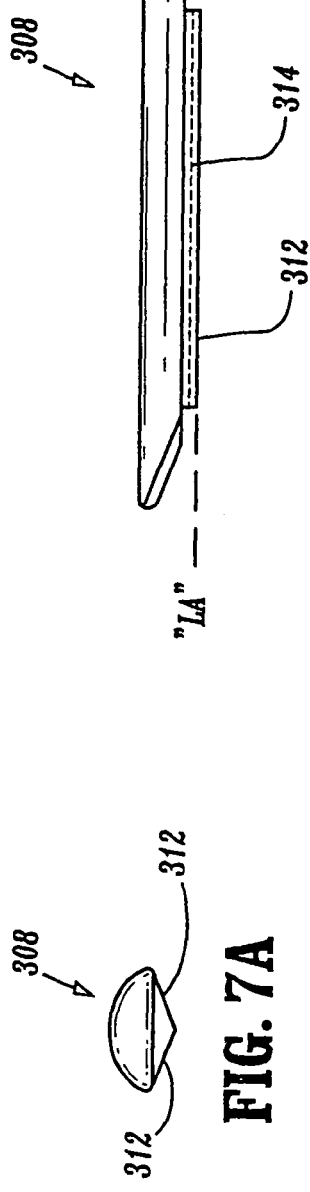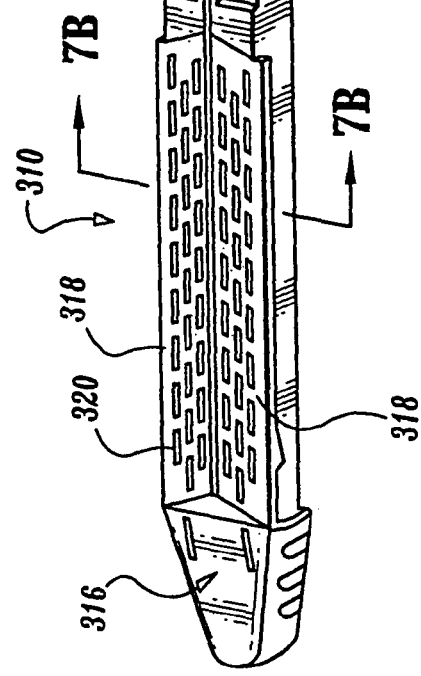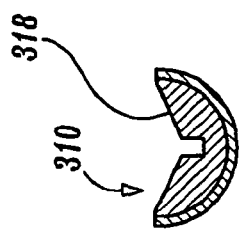

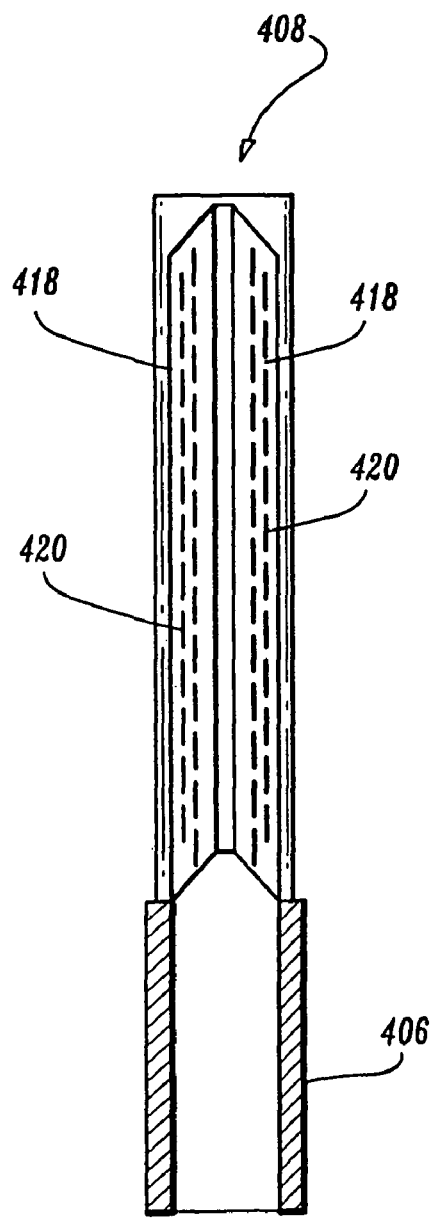 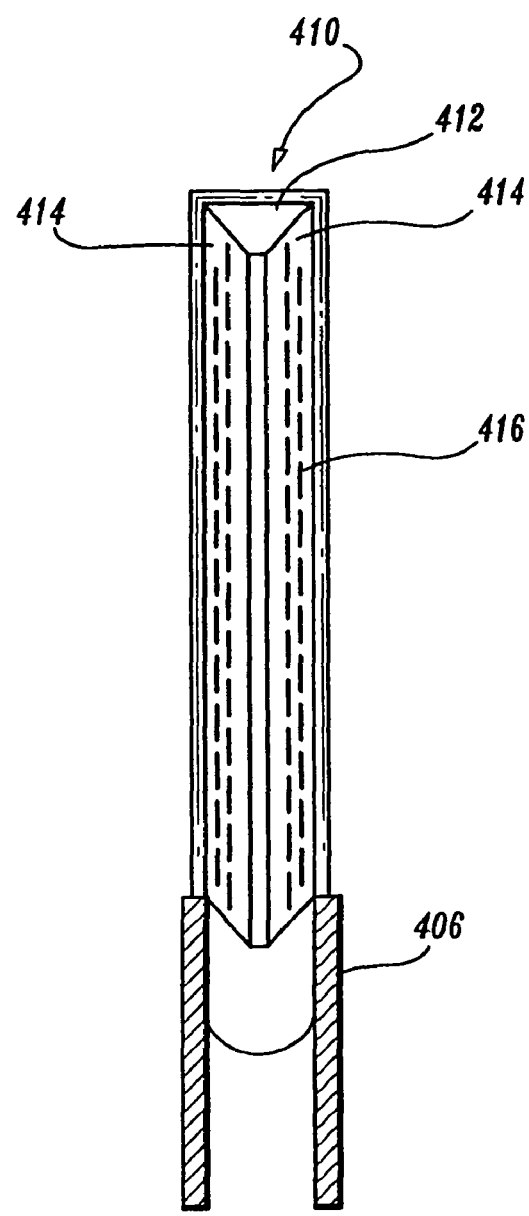
FIG. 9a  FIG. 9b

SURGICAL STAPLING APPARATUS INCLUDING AN ANVIL AND CARTRIDGE EACH HAVING COOPERATING MATING SURFACES

CROSS REFERENCE TO RELATED APPLICATIONS

This application is a continuation of U.S. patent application Ser. No. 11/113,928 filed Apr. 25, 2005, which is a continuation of application Ser. No. 10/411,686 filed Apr. 11, 2003, now U.S. Pat. No. 7,070,083 which claims benefit of U.S. Provisional Application Ser. No. 60/372,356 filed Apr. 11, 2002. Each of which the disclosures are incorporated herein in their entirety by this reference.

BACKGROUND

1. Technical Field

The present disclosure relates to surgical stapling apparatus, and more particularly to surgical stapling apparatus having complementarily shaped staple anvil and staple cartridge surfaces.

2. Background of Related Art

There are several known types of surgical staplers specifically adapted for use in various procedures such as end-to-end anastomosis; circular end-to-end anastomosis; gastrointestinal anastomosis; endoscopic gastrointestinal anastomosis; and transverse anastomosis specific examples of staplers for these various procedures are for example, EEA™, CEEA™, GIA™, EndoGIA™, and TA™ available from United States Surgical a division of Tyco Health-Care Group, LP, Norwalk, Conn., with each stapler including an anvil which is adjustably approximated relative a staple cartridge. The staple cartridge typically has at least two laterally spaced rows of staples, which depending on the particular stapler may be arranged in a linear or non-linear fashion. The anvil includes staple deforming depressions formed therein which staple deforming depressions are aligned with the rows of staples in the cartridge. In use, each of the surgical staplers involves the gripping of tissue to be fastened, the ejecting of individual staples, the forcing of staples through the gripped tissue and the closing of the staples against the staple deforming depressions formed in the anvil of the stapler.

A continuing need exists for improved surgical stapling apparatus having means for enhancing alignment of the anvil with the staple cartridge in one of, preferably in both, a transverse and longitudinal direction during or upon approximation or mating of the anvil with the staple cartridge with tissue or material to be stapled therebetween.

SUMMARY

The present disclosure relates to surgical stapling apparatus having a shaped anvil and shaped cartridge.

According to one aspect of the present disclosure, a surgical stapling apparatus is provided including an anvil having a working surface with a plurality of staple forming depressions formed therein, the working surface of the anvil having a non-planar cross-sectional shape, and a staple cartridge having a working surface in juxtaposition to the working surface of the anvil and including a plurality of staple retention slots formed therein, the working surface of the staple cartridge having a shape which complements the shape of the working surface of the anvil, wherein when the anvil and staple cartridge are approximated with one another with tissue therebetween, at least a portion of the working surface of the anvil cooperates with at least a portion of the working surface of the staple cartridge to enhance alignment of the plurality of staple forming depressions with the plurality of staple retention slots.

It is envisioned that the working surface of the staple cartridge includes a pair of inclined wall portions extending longitudinally along a length thereof, and wherein the working surface of the anvil includes a pair of inclined wall portions extending along a length thereof and complementing the pair of inclined wall portions of the working surface of the staple cartridge. Each inclined wall portion of the staple cartridge has an inner longitudinal edge and an outer longitudinal edge, and the inner longitudinal edges are parallel and spaced apart from one another, recessed with respect to a plane defined by the outer longitudinal edges, and defining a knife track.

It is envisioned that the staple cartridge includes first and second side walls, parallel to and spaced apart from one another, and wherein a first inclined wall portion of the staple cartridge extends from the first side wall of the staple cartridge at an angle which is less than 90° relative to the first side wall and a second inclined wall portion of the staple cartridge extends from the second side wall of the staple cartridge at an angle which is less than 90° relative to the second side wall. Each inclined wall portion of the anvil has an inner longitudinal edge and an outer longitudinal edge, and the inner longitudinal edges are parallel and spaced apart from each other, recessed with respect to a plane defined by the outer longitudinal edges, and defining a knife track.

It is envisioned that the anvil includes first and second side walls, parallel to and spread apart from one another, and wherein a first inclined wall portion of the anvil extends from the first side wall of the anvil at an angle which is greater than 90° and less than 180° relative to the first side wall and a second inclined wall portion of the staple cartridge extends from the second side wall of the anvil at an angle which is greater than 90° and less than 180° relative to the second side wall.

The working surface of the staple cartridge can have an arcuate shape in a direction transverse to a longitudinal axis thereof, and wherein the working surface of the anvil has a shape which is complementary to the arcuate surface of the staple cartridge. It is envisioned that the working surface of the staple cartridge is one of concave and convex in the transverse direction.

It is contemplated that at least one of the staple cartridge and the anvil includes a longitudinally running channel extending along the length thereof.

In one embodiment it is envisioned that the working surfaces of the anvil and the staple cartridge are annular. The staple cartridge can include an upstanding annular side wall extending from at least one of an inner and outer terminal edge of the surface of the staple cartridge and inclined at an obtuse angle relative thereto. Alternatively, the staple cartridge can include an upstanding annular side wall extending from each of an inner edge and an outer edge of the surface of the staple cartridge, wherein the annular side walls are inclined at an obtuse angle relative to the surface of the surgical staple cartridge. The angle of inclination of the annular side walls is greater than 90° and less than 180°.

It is envisioned that the working surface of the anvil can have an arcuate shape in a radial direction and wherein the working surface of the staple cartridge has a shape that is complementary to that of the working surface of the anvil. Preferably, the working surface of the anvil, in radial transverse cross-section, is one of convex and concave.

It is contemplated that the working surface of the anvil is angled such that an inner terminal edge thereof is depressed relative to an outer terminal edge thereof. Alternatively, it is contemplated that the working surface of the anvil is angled such that an inner terminal edge thereof is elevated relative to an outer terminal edge thereof.

It is envisioned that the working surface of the anvil is provided with at least one longitudinally oriented arcuate recess formed therein and wherein the working surface of the staple cartridge is provided with at least one projection extending therefrom, wherein the at least one projection complements the at least one recess to longitudinally align the anvil and staple cartridge when approximated with one another.

According to another aspect of the present disclosure, a surgical stapling apparatus is provided which includes an anvil having a working surface with a shaped topography, and a staple cartridge having a working surface in juxtaposition with the anvil, the working surface of the staple cartridge having a shaped topography which is complementary to the shaped topography of the working surface of the shaped anvil, such that when the anvil and the staple cartridge are approximated with one another with tissue therebetween, cooperation of at least a portion of the working surface of the anvil with at least a portion of the working surface of the staple cartridge enhances alignment of the staple cartridge and the anvil in at least one of transverse and longitudinal directions.

It is envisioned that either the anvil, the staple cartridge or both the anvil and the staple cartridge can have an arcuate cross-sectional profile or a V-shaped cross-sectional profile. It is further envisioned that at least one of the anvil and the staple cartridge has a topographical surface undulating in at least one of a transverse and a longitudinal direction.

In one embodiment, at least one of the anvil and staple cartridge defines a longitudinal axis. The working surface of the anvil is angled with respect to the longitudinal axis of the anvil. The working surface of the anvil can be angled to either decline or incline from the distal end to the proximal end of the anvil. It is envisioned that the anvil can have at least one of a V-shaped and arcuate transverse cross-sectional profile.

In another embodiment, the surgical stapling apparatus defines a longitudinal axis. It is thus contemplated that the working surface of each of the anvil and staple cartridge is angled relative to the longitudinal axis of the surgical stapling apparatus. The working surface of the anvil can be angled to either decline or incline from the distal end to the proximal end of the anvil. It is envisioned that the anvil can have at least one of a V-shaped and arcuate transverse cross-sectional profile.

In accordance with another aspect of the present disclosure, a surgical stapling apparatus is provided including an anvil having a working surface with a plurality of staple forming depressions formed therein, the working surface of the anvil having a non-planar cross-sectional shape, and a staple cartridge having a working surface in juxtaposition to the working surface of the anvil and including a plurality of staple retention slots formed therein. The working surface of the staple cartridge has a shape which complements the shape of the working surface of the anvil, such that as the anvil and staple cartridge are approximated relative to one another with tissue therebetween, the working surface of the anvil cooperates with the working surface of the staple cartridge to help align the plurality of staple forming depressions with the plurality of staple retention slots.

In yet another aspect of the present disclosure, a surgical stapling apparatus is provided including an anvil having a working surface with a shaped topography, and a staple cartridge having a working surface in juxtaposition with the anvil. The working surface of the staple cartridge has a shaped topography which is complementary to the shaped topography of the working surface of the shaped anvil, such that as the anvil and the staple cartridge are approximated with one another with tissue therebetween, cooperation of at least a portion of the working surface of the anvil with at least a portion of the working surface of the staple cartridge enhances alignment of the staple cartridge and the anvil in at least one of a transverse and longitudinal direction.

It is envisioned that, when approximated, the anvil and cartridge of the surgical stapling apparatus can be clamped.

These objects together with other objects of the disclosure, along with the various features of novelty which characterize the disclosure, are pointed out with particularity in the claims annexed to and forming a part of the disclosure.

BRIEF DESCRIPTION OF THE DRAWINGS

By way of example only, preferred embodiments of the disclosure will be described with reference to the accompanying drawings, in which:

FIG. 7 is an enlarged exploded perspective view of a tool assembly for the surgical stapling apparatus shown in FIG. 6 including the staple cartridge and staple anvil in accordance with the present disclosure;

FIG. 7A is a distal end view of the staple anvil of FIG. 7;

FIG. 7B is a cross-sectional view of the staple cartridge of FIG. 7 as taken along 7B-7B of FIG. 7;

FIG. 9A is a plan view of the staple anvil of the surgical stapling apparatus of FIG. 8;

FIG. 9B is a plan view of the staple cartridge of the surgical stapling apparatus of FIG. 8;

DETAILED DESCRIPTION OF PREFERRED EMBODIMENTS

Figure 1:
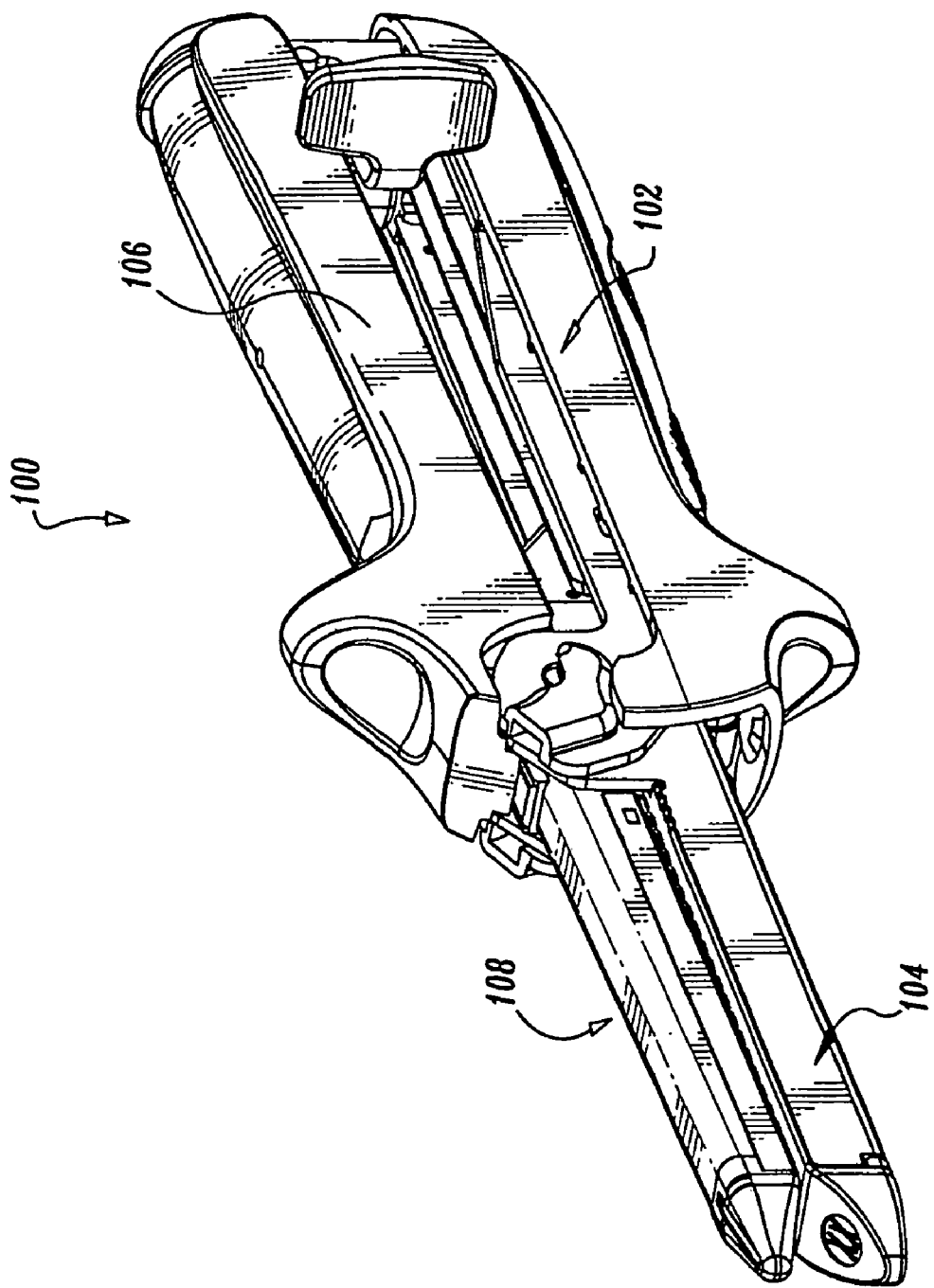
FIG. 1 is a perspective view of one illustrative embodiment of a linear surgical stapling apparatus constructed in accordance with the present disclosure.
Figure 2:
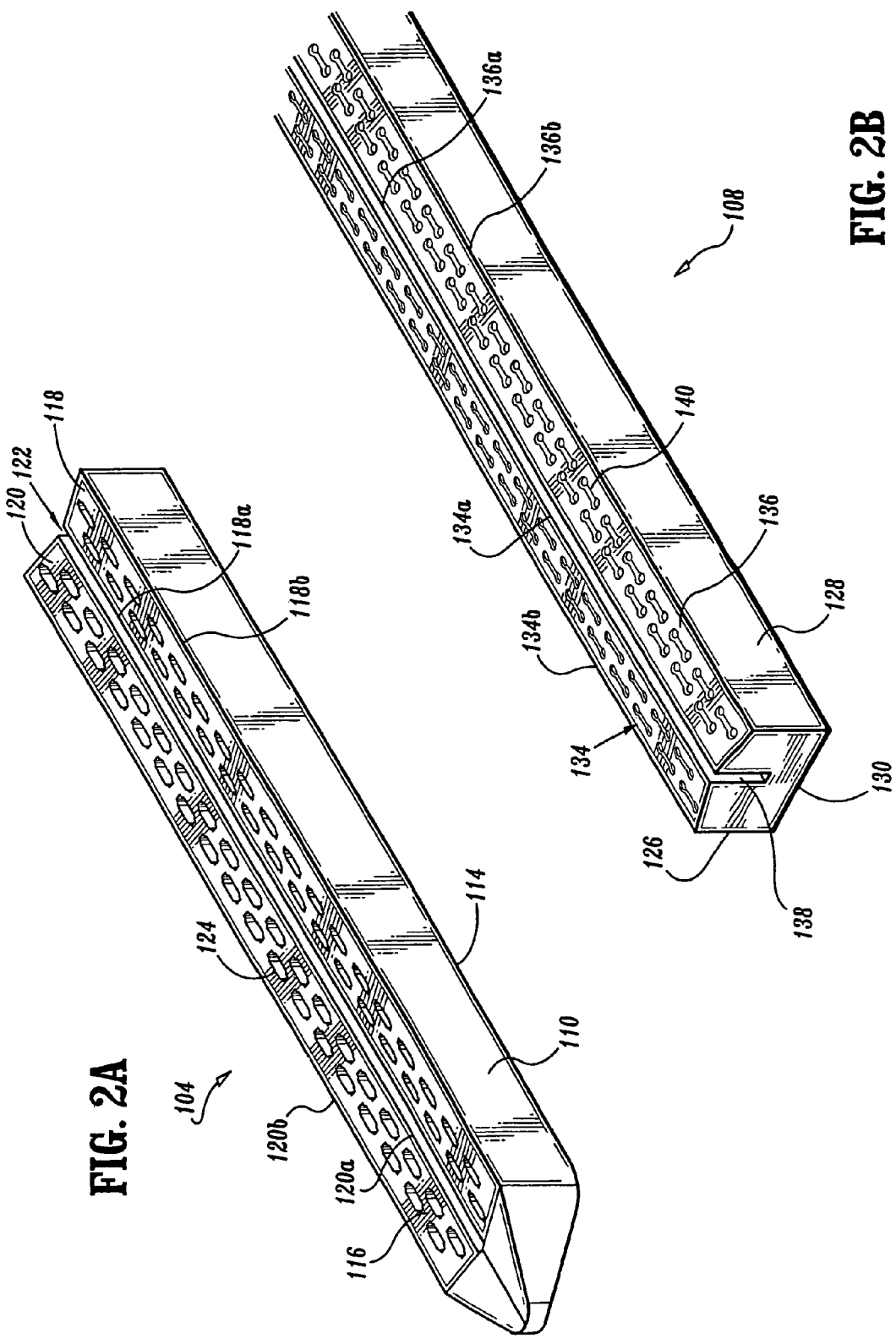
FIG. 2A is an enlarged perspective view of one embodiment of a linear staple cartridge for a surgical stapling apparatus such as the apparatus shown in FIG. 1.
FIG. 2B is an enlarged perspective view of a staple anvil for use with the staple cartridge of FIG. 2A.

Preferred embodiments of the presently disclosed surgical stapling apparatus will now be described in detail with reference to the drawing figures wherein like reference numerals identify similar or identical elements. In the drawings and in the description which follows, the term "proximal", as is traditional, will refer to the end of the surgical apparatus which is closest to the operator, while the term "distal" will refer to the end of the device which is furthest from the operator.

Referring now in detail to FIGS. 1-5, in which like reference numerals identify similar or identical elements, a surgical stapling instrument or apparatus in accordance with a first embodiment of the disclosure is generally designated as 100. Surgical stapling instrument 100 is an open gastro-intestinal anastomosis type stapler and includes a first handle 102 having a jaw defining a staple cartridge 104 extending from a distal end thereof, and a second handle 106 having a jaw defining a staple anvil 108 extending from a distal end thereof, such that staple cartridge 104 is substantially aligned with staple anvil 108.

Figure 3:
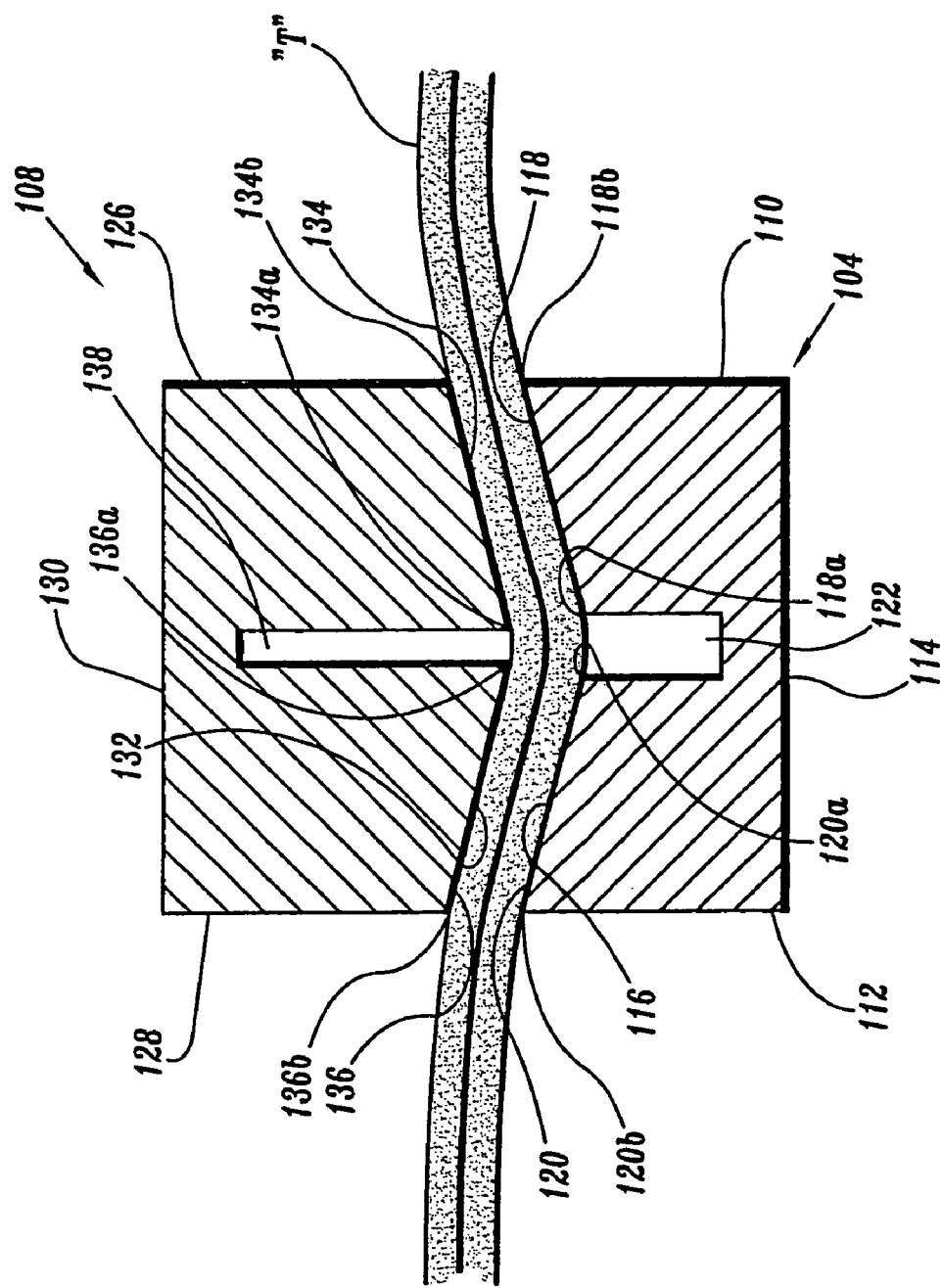
FIG. 3 is a schematic enlarged cross-sectional view of the approximated staple cartridge and staple anvil of FIGS. 2A and 2B.
Figure 4:
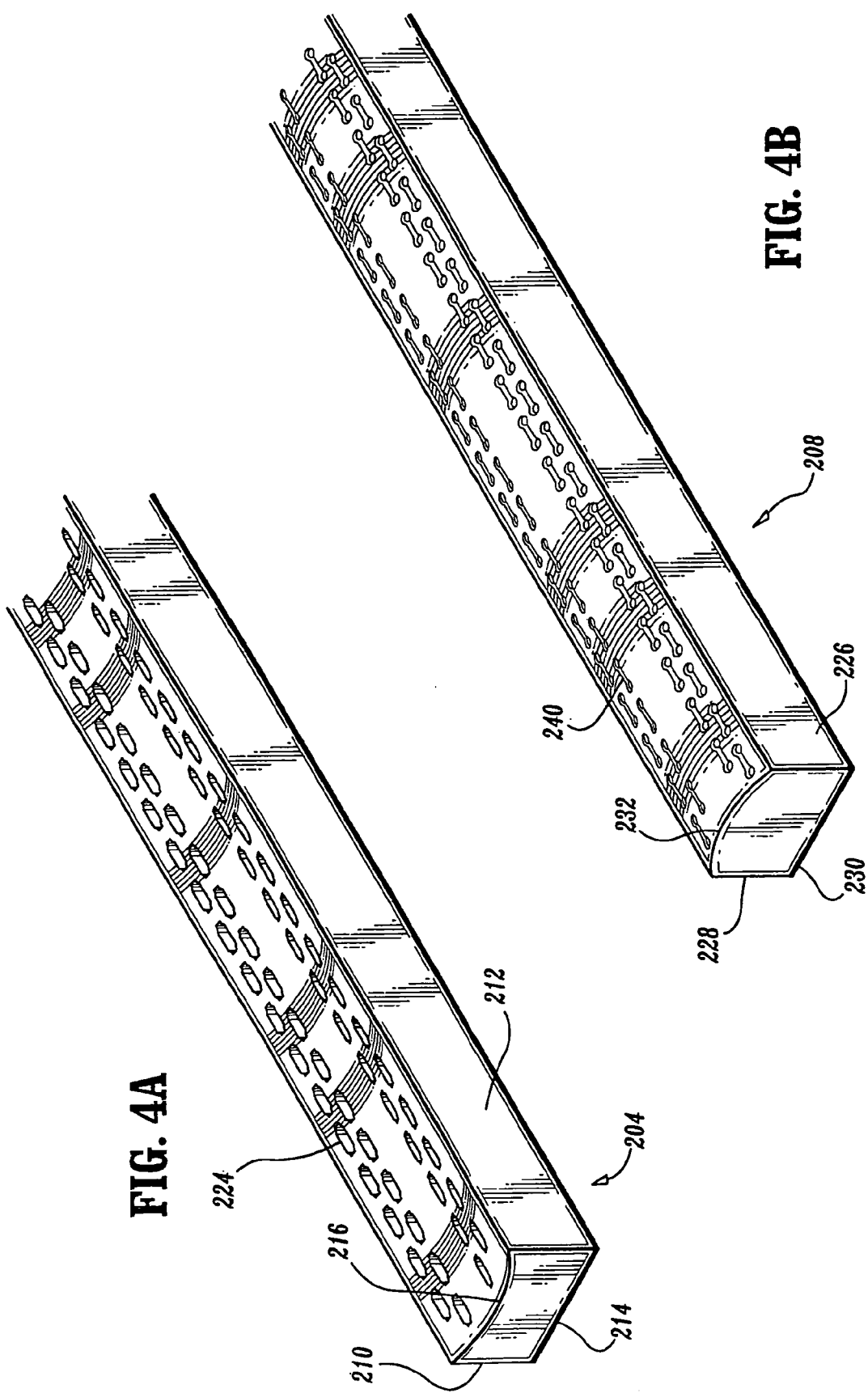
FIG. 4A is an enlarged perspective view of an alternative illustrative embodiment of a staple cartridge for a linear surgical stapling apparatus.
FIG. 4B is an enlarged perspective view of an alternative illustrative embodiment of a staple anvil for use with the staple cartridge of FIG. 4A.

Turning now to FIGS. 2A, 2B and 3, enlarged sections of the staple cartridge 104 and staple anvil 108 are shown, respectively. As seen in particular in FIGS. 2A and 3, staple cartridge 104 includes a pair of parallel spaced side walls 110 and 112 (see FIG. 3), a planar bottom wall 114, and a dual inclined top wall 116 (according to the orientation of staple cartridge 104 of FIG. 3) defining a working surface. Preferably dual inclined top wall 116 is inclined in a direction transverse to and away from the longitudinal axis. Dual inclined top wall 116 includes a first inclined top wall portion 118 inclined at an angle less than 90° relative to and toward first side wall 110, and a second inclined top wall portion 120 inclined at an angle less than 90° relative to and toward second side wall 112. Each inclined wall portion 118, 120 includes and inner terminal edge 118a, 120a, respectively, and an outer terminal edge 118b, 120b, respectively. In other words, inner terminal edge 118a, 120a are recessed into staple cartridge 104 with respect to a plane defined by outer terminal edges 118b, 120b. Each of the first and second inclined top wall portions 118, 120 includes a pair of rows of laterally spaced staple retention slots 124, extending substantially the entire length of staple cartridge 104, for receiving a plurality of fasteners (e.g., staples) and pushers therein (both of which are not shown). It is envisioned that staple cartridge 104 further includes a longitudinally oriented central passageway 122 extending the length thereof.

As seen in particular in FIGS. 2B and 3, staple anvil 108 includes a pair of parallel spaced side walls 126 and 128, a planar top wall 130, and a dual inclined bottom wall 132 (according to the orientation of staple anvil 108 of FIG. 3) defining a working surface. Preferably, dual inclined bottom wall 132 is inclined in a direction transverse to the longitudinal axis. Dual inclined bottom wall 132 includes a first inclined bottom wall portion 134 inclined toward the longitudinal axis at an angle greater than 90° and less than 180° relative to first side wall 126, and a second inclined bottom wall portion 136 inclined toward the longitudinal axis at an angle greater than 90° and less than 180° relative to second side wall 128. Staple anvil 108 further includes a longitudinally oriented passageway 138 extending the length of staple anvil 108. Each inclined wall portion 134, 136 includes an inner terminal edge 134a, 136a, respectively, and an outer terminal edge 134b, 136b, respectively. In other words, inner terminal edges 118a, 120a are elevated out of staple anvil 108 with respect to a plane defined by outer terminal edges 134b, 136b. Each of the first and second inclined bottom wall portions 134, 136 includes a pair of laterally spaced rows of anvil depressions 140. Preferably, anvil depressions 140 of staple anvil 108 are in juxtaposed alignment with staple retentions slots 124 of staple cartridge 104.

Preferably, the angle of inclination of first inclined top wall portion 118 of staple cartridge 104 is complementary to the angle of inclination of first inclined bottom wall portion 134 of staple anvil 108. Similarly, the angle of inclination of second inclined top wall portion 120 of staple cartridge 104 is complementary to the angle of inclination of second inclined bottom wall portion 136 of staple anvil 108. In this manner, as staple cartridge 104 is approximated relative to staple anvil 108, a camming action takes place between the inclined surfaces (i.e., inclined top wall portions 118, 120) of staple cartridge 104 and the inclined surfaces (i.e., inclined bottom wall portions 134, 136) of staple anvil 108. As such, when staple cartridge 104 is approximated relative to or with staple anvil 108 with tissue "T" therebetween, alignment of retention slots 124 with corresponding anvil depressions 140 is enhanced. The configurations of staple cartridge 104 and staple anvil 108 help align retention slots 124 and anvil depressions 140 with one another as staple cartridge 104 and staple anvil 108 are brought into approximation or mating relationship with one another with tissue "T" and/or material to be stapled therebetween, and each time staple cartridge 104 is approximated with staple anvil 108 with tissue "T" and/or material to be stapled therebetween.

"Approximated" herein means that the working surfaces of the anvil and cartridge are sufficiently close or near to each other and in contact with tissue, if there is tissue therebetween, that staples can be fired from the slots of the staple cartridge and properly formed in the depressions of the anvil. To be approximated the anvil and cartridge need not be, but preferably are, clamped or otherwise held together. Approximated may also apply to surgical stapling instruments which employ two-part fasteners wherein a first part of the two-part fastener is stored in a cartridge or like member and can be fired and properly joined to a second part of the two-part fastener disposed in an anvil or like member.

While it has been described that the angle of inclination of the dual inclined top wall 116 and the dual inclined bottom wall 132 are relative to parallel side walls 110, 112 and 126, 128 of staple cartridge 104 and staple anvil 108, respectively, it is envisioned that the angle of inclination can be relative to any fixed reference. It is also envisioned that the angle of inclination of first and second inclined top wall portions 118, 120 of staple cartridge 104 is inclined at an angle which is greater than 90° relative to side walls 110, 112 while the angle of inclination of first and second inclined bottom wall portions 134, 136 of staple anvil 108 is inclined at an angle less than 90° relative to side walls 126, 128. Preferably, the angle of inclination of top wall portions 118, 120 complements the angle of inclination of bottom wall portions 134, 136.

As seen more clearly in FIG. 3, first and second inclined top wall portions 118, 120 of staple cartridge 104 are inclined such that the longitudinal edges of each of inclined bottom wall portions 118, 120, defining longitudinal passageway 122, are closer to planar bottom wall 114 than are the longitudinal edges of the inclined top wall portions 118, 120 which are in contact with each of side walls 110, 112, respectively. Correspondingly, first and second inclined top wall portions 134, 136 of staple anvil 108 are inclined such that the longitudinal edges of each of inclined bottom wall portions 134, 136, defining longitudinal passageway 138, are further away from top planar wall 130 than are the longitudinal edges of inclined top wall portions 134, 136 which are in contact with each of side walls 126, 128, respectively. Once again, while it is shown that first and second inclined top wall portions 118, 120 are inclined toward bottom planar surface 114 with first and second inclined bottom wall portions 134, 136 inclined away from top planar surface 130, it is envisioned that first and second inclined top wall portions 118, 120 can be inclined away from the bottom planar surface 114 while first and second inclined bottom wall portions 134, 136 are inclined toward top planar surface 130.

As will be described in greater detail below, it is contemplated that first and second top wall portions 118, 120 can be either declining or inclining from a distal end or distal end portion to a proximal end or proximal end portion while first and second bottom wall portions 134, 136 are declining or inclining in a direction and at an angle equal and opposite to top wall portions 118, 120. It is further contemplated that one of first and second top wall portions 118, 120 can be declining in a longitudinal direction while the other of first and second wall portions 118, 120 is inclining in a longitudinal direction. Concomitantly, first and second wall portions 134, 136 is declining or inclining in a longitudinal direction which complements the longitudinally inclining or declining first and second top wall portions 118, 120.

Figure 5:
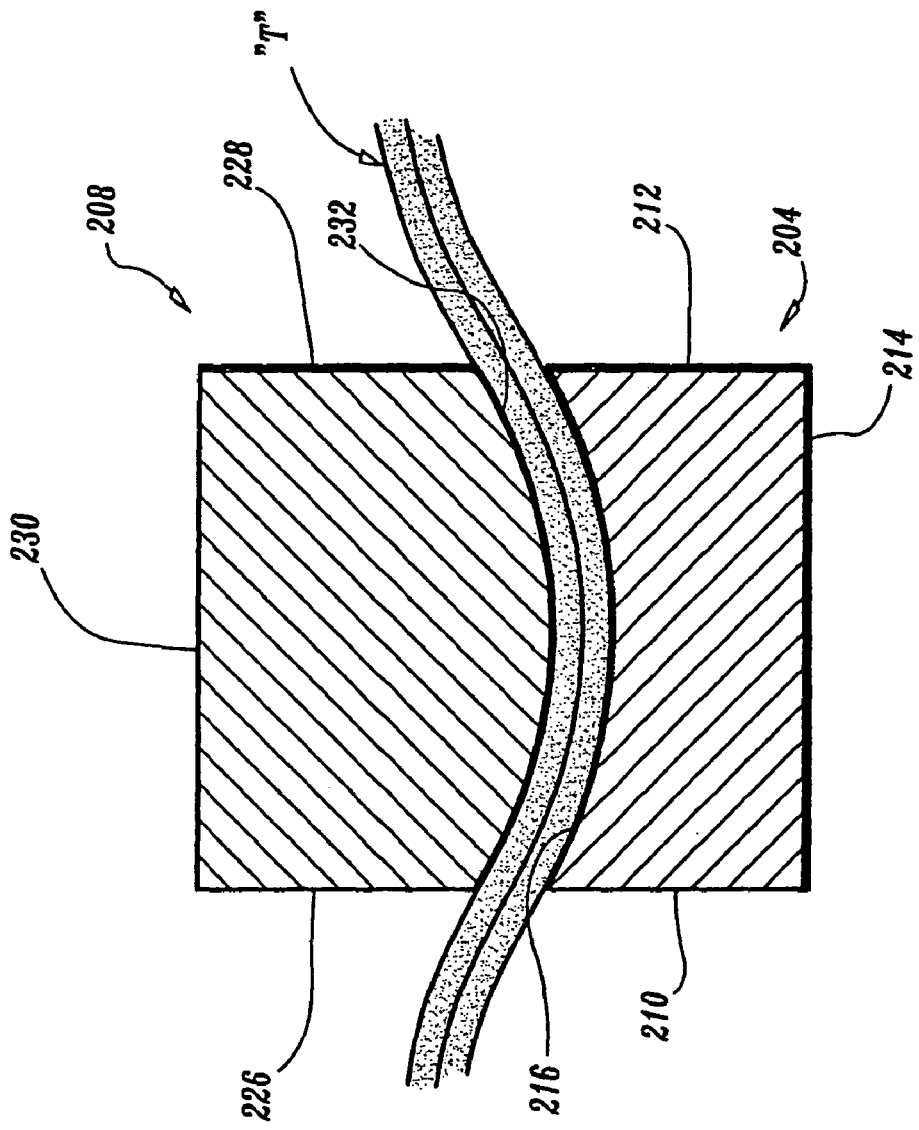
FIG. 5 is an enlarged cross-sectional view of the approximated staple cartridge and staple anvil of FIGS. 4A and 4B.

Turning now to FIGS. 4A, 4B and 5, an enlarged perspective view of an alternative staple cartridge 204 and an alternative staple anvil 208 are shown. Staple cartridge 204 includes a pair of parallel spaced side walls 210 and 212, a planar bottom wall 214 and a top wall 216 (according to the orientation of staple cartridge 204 of FIG. 5) which is arcuate, preferably semi-circular, in a direction transverse to a longitudinal axis thereof defining a working surface. Preferably, top wall 216 is concave. Concave top wall 216 includes a pair of laterally spaced rows of staple retention slots 224 extending the entire length of staple cartridge 204. Staple anvil 208 includes a pair of parallel spaced side walls 226 and 228, a planar top wall 230 and a bottom wall 232 (according to the orientation of staple anvil 208 of FIG. 5) which is arcuate, preferably semi-circular, in a direction transverse to the longitudinal axis thereof defining a working surface. Preferably, bottom wall 232 is convex. Convex bottom wall 232 of staple anvil 208 includes a pair of laterally spaced rows of staple forming depressions 240. It is contemplated that top wall 216 and bottom wall 232 can also be arcuate (e.g., semi-circular) in a direction longitudinally transverse to the longitudinal axis thereof.

Preferably, the radius of curvature of concave top wall 216 of staple cartridge 204 is substantially equal to the radius of curvature of convex bottom wall 232 of staple anvil 208. In this manner, as staple cartridge 204 and staple anvil 208 are brought into approximation or are approximated with one another with tissue "T" therebetween, a camming action takes place between concave top wall 216 of staple cartridge 204 and convex bottom wall 232 of staple anvil 208 to thereby help align the rows of staple retention slots 224 of staple cartridge 204 with the rows of staple forming depressions 240 of staple anvil 208.

As seen more clearly in FIG. 5, concave top wall 216 of staple cartridge 204 is adapted to complement convex bottom wall 232 of staple anvil 208 therein upon approximation of staple cartridge 204 with staple anvil 208 with tissue "T" therebetween. Accordingly, alignment of staple retention slots 224 of cartridge 204 with staple forming depressions 240 formed in anvil 208 is enhanced. While the convex surface is shown as bottom wall 232 of staple anvil 208 and concave surface is shown as top wall 216 of staple cartridge 204, it is envisioned that the convex surface can project from the top wall of staple cartridge 204 while concave surface can project into the bottom wall of staple anvil 208.

It is envisioned that staple cartridge 204 and/or staple anvil 208 include a longitudinally oriented central channel formed therethrough. It is envisioned that the central channel can accommodate a knife disposed within the staple cartridge and be slidable along the length of the central channel.

Reference can be made to commonly assigned U.S. Pat. No. 6,045,560 to McKean et al., U.S. Pat. No. 6,032,849 to Mastri et al., and U.S. Pat. No. 5,964,394 to Robertson, the entire contents of which are incorporated herein by reference, for a more detailed explanation of the operation of surgical stapling instrument 100 and for approximating the staple cartridge with the staple anvil.

Figure 6:
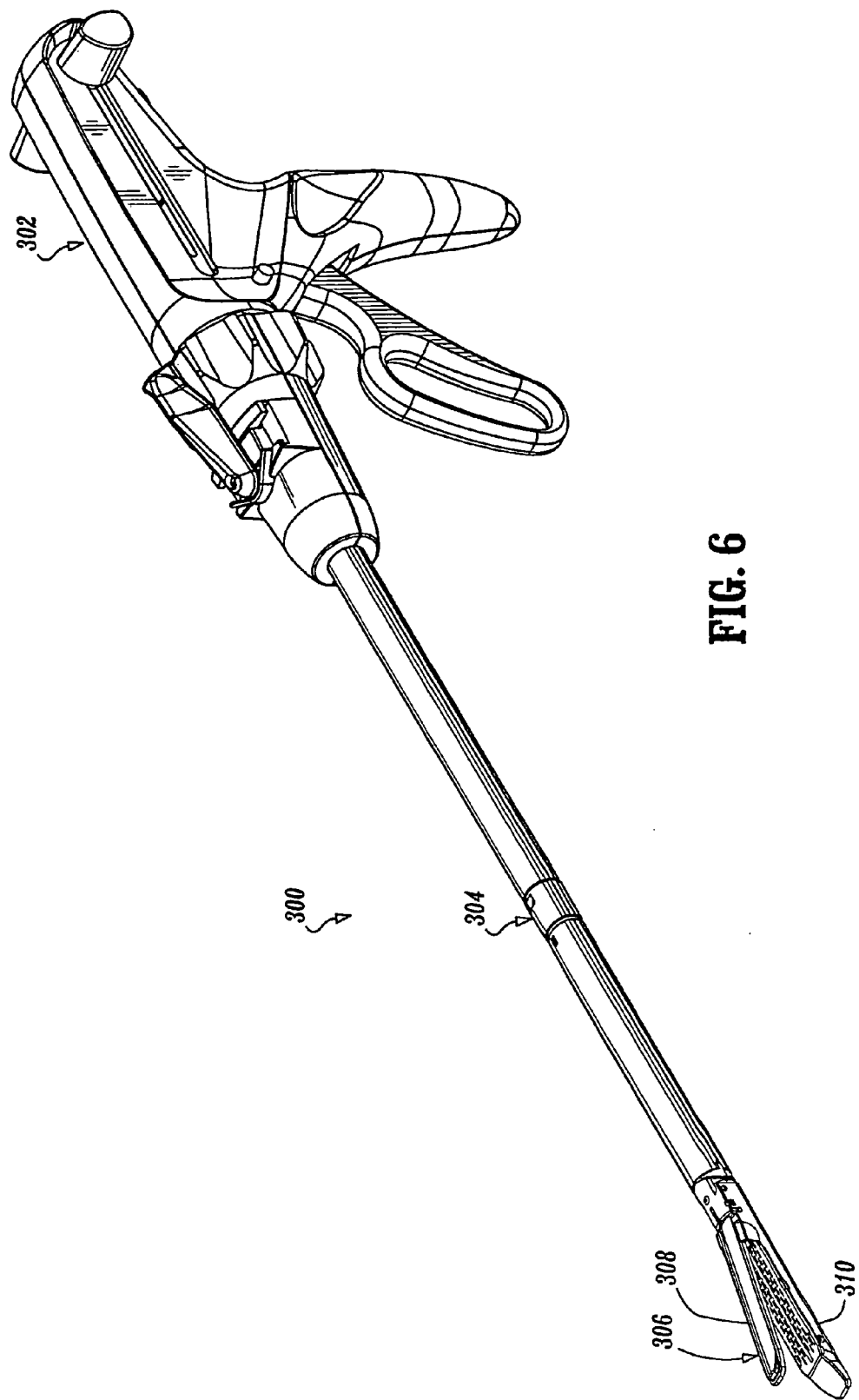
FIG. 6 is a perspective view of an alternative surgical stapling apparatus including a staple cartridge and staple anvil in accordance with the present disclosure.

Turning now to FIGS. 6-7B, there is disclosed a laparoscopic stapling apparatus (i.e., of the type such as an "Endo GIA™" surgical stapling apparatus available from United States Surgical, a division of Tyco Healthcare Group, LP, Norwalk, Conn.) generally shown as 300 and including a staple cartridge and staple anvil in accordance with the present disclosure. In general, the laparoscopic stapler includes a handle 302, an operative tool 306 (i.e., end effector) and an elongated shaft 304 for interconnecting operative tool 306 to handle 302. In general, operative tool 306 is designed to approximate and then to staple and divide tissue "T" held therebetween. Accordingly, as seen in FIG. 7, operative tool 306 is a pair of opposed jaws including a staple anvil 308 and a staple cartridge 310 couplable, e.g., pivotally or transversely, to one another.

In particular, as seen in FIG. 7A, staple anvil 308 is an elongated arm-like structure having a pair of inclined lower surfaces 312 which project outwardly along and away from a central longitudinal axis "LA" of staple anvil 308. Preferably, inclined lower surfaces 312 are inclined in a direction transverse to the longitudinal axis. Each of inclined surfaces 312 of staple anvil 308 is provided with a plurality of staple forming depressions 314, preferably a pair of laterally spaced rows of anvil depressions 140. Staple cartridge 310 is also an elongated arm-like member adapted to receive a removable staple cartridge assembly 316 therein. Staple cartridge assembly 316 includes a pair of inclined upper surfaces 318 projecting outwardly from and along a central longitudinal axis of staple cartridge assembly 316 and defining a working surface. Preferably, each of inclined upper surfaces 318 is inclined in a direction transverse to the longitudinal axis. Each of inclined upper surfaces 318 of staple cartridge assembly 316 includes a pair of laterally spaced rows of staple retention slots 320. The cooperation of the complementary working surfaces with tissue therebetween, helps to align staple retention slots 320 of staple cartridge assembly 316 with staple forming depressions 314 of staple anvil 308 when staple cartridge assembly 316 is being or is approximated with staple anvil 308 when the working surfaces have tissue "T" therebetween.

Inclined lower surfaces 312 of staple anvil 308 have an angle of inclination which complements an angle of inclination of inclined upper surfaces 318 of staple cartridge assembly 316. In this manner, when staple anvil 308 is, e.g., lowered or otherwise brought into contact with tissue "T" between the working surfaces of anvil 308 and staple cartridge assembly 316, a camming action between inclined lower surfaces 312 and inclined upper surfaces 318 helps align staple forming depressions 314 of staple anvil 308 with staple retention slots 320 of staple cartridge assembly 316. While the angle of inclination of upper surfaces 318 of staple cartridge assembly 316 have been shown as projecting inward and the angle of inclination of lower surfaces 312 of staple anvil 308 have been shown to project outward, it is envisioned that the angle of inclination of surfaces 312 and 318 can be reversed. While generally planar inclined surfaces have been described, it is envisioned that the inclined surfaces can be replaced with arcuate surfaces in the manner disclosed in FIGS. 4A, 4B and 5 without departing from the breath of the disclosure.

Reference can be made to commonly assigned U.S. Pat. Nos. 6,330,965 and 6,241,139 to Milliman et al., the entire contents of which are incorporated herein by reference, for a more detailed explanation of the operation of surgical stapling apparatus 300 and of the approximation of the staple cartridge with the staple anvil.

Figure 8:
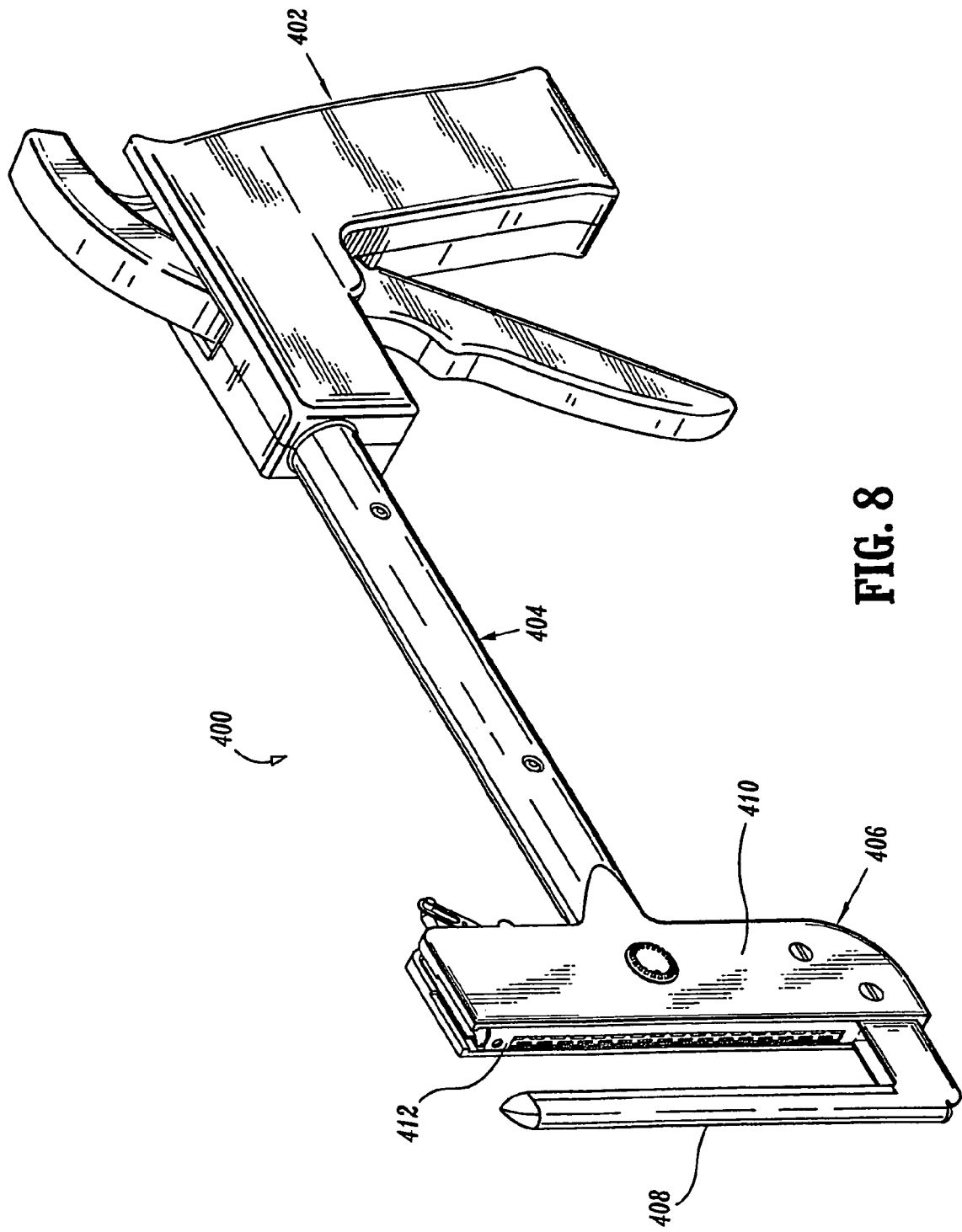
FIG. 8 is a perspective view of an alternative surgical stapling apparatus including a staple cartridge and staple anvil in accordance with the present disclosure.
Figure 10:
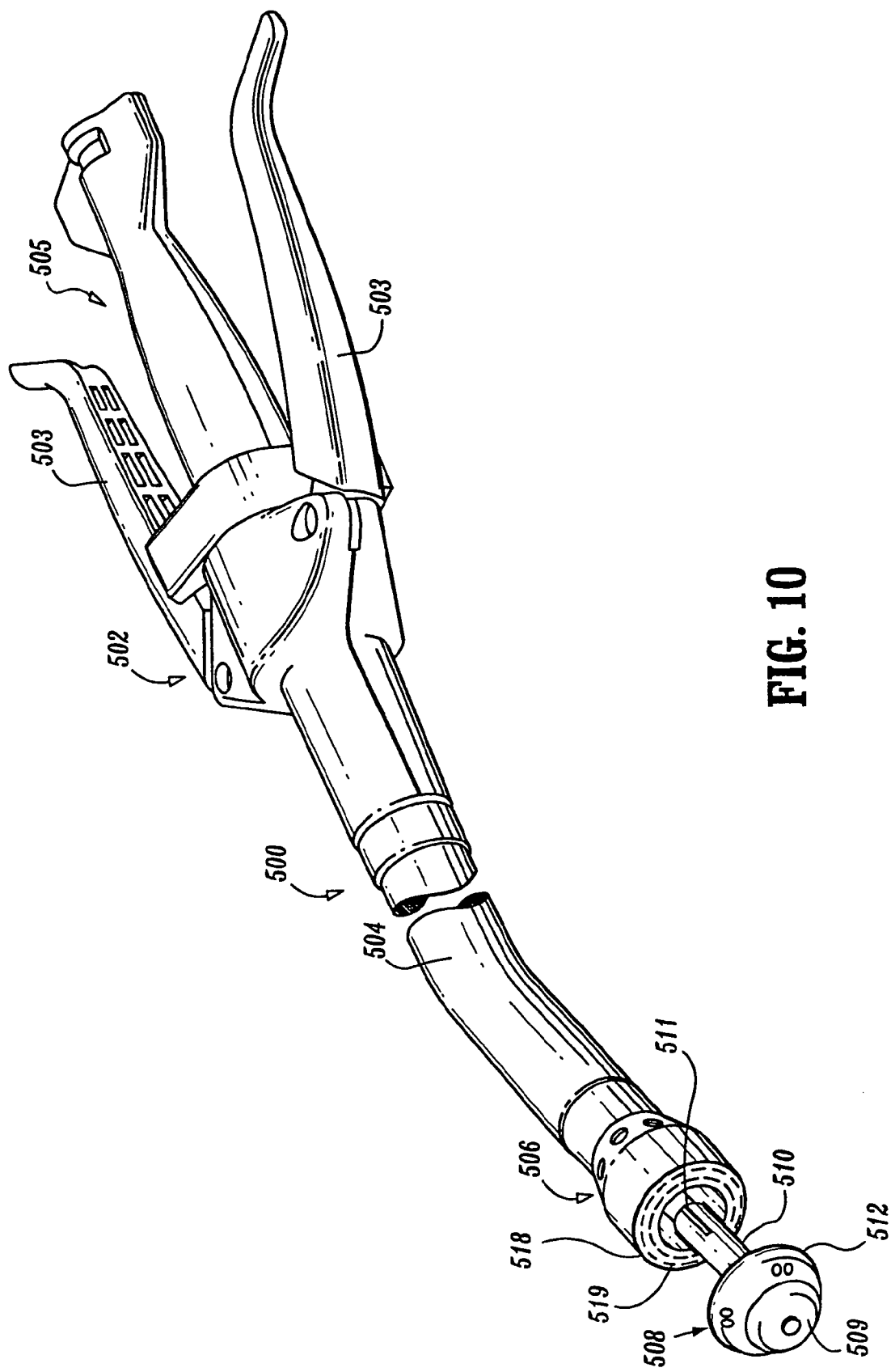
FIG. 10 is a perspective view of an alternative surgical stapling apparatus including a staple cartridge and staple anvil in accordance with the present disclosure.
Figure 11A:
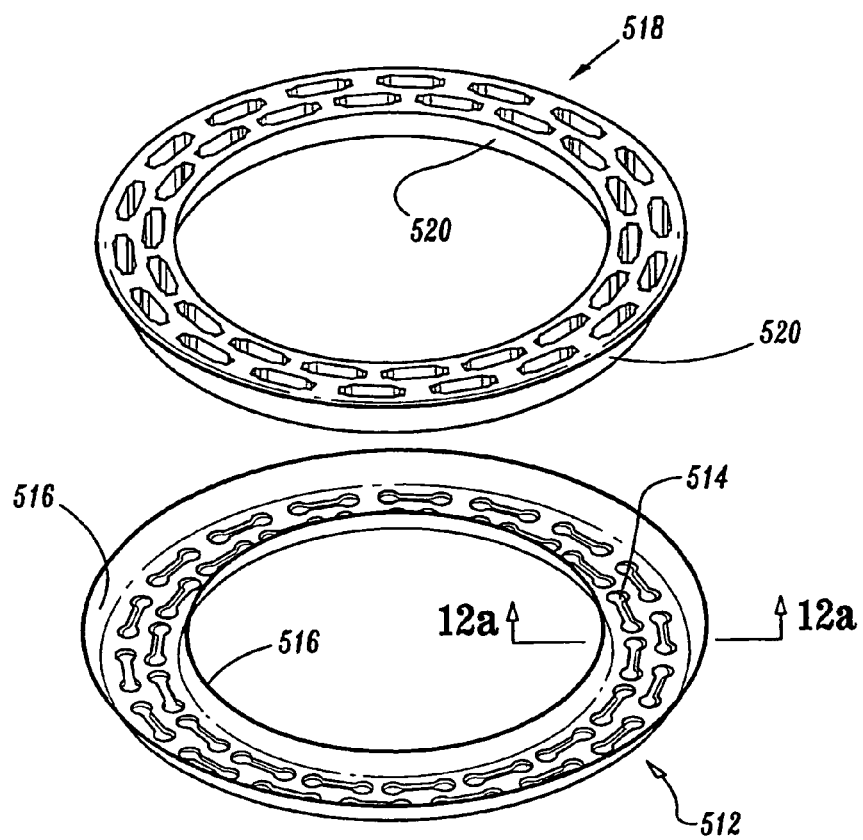
FIG. 11A is an exploded perspective view of the staple cartridge and staple anvil working surfaces in accordance with the present disclosure.
Figure 11B:
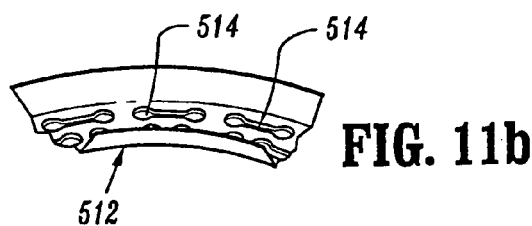
FIG. 11B is a perspective view of the staple cartridge of FIG. 11A.
Figure 11C:
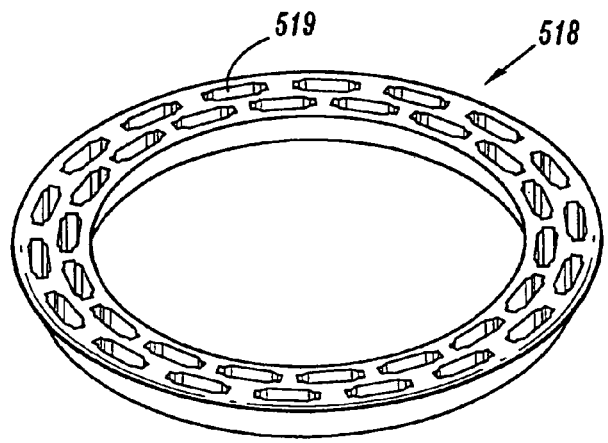
FIG. 11C is a perspective view of the staple anvil of FIG. 11A.

FIG. 8 discloses an alternative stapling apparatus of the transverse anastomosis type for stapling a patient's mesentery or omentum (i.e., such as a "TA™" type surgical stapling apparatus available from United States Surgical, a division of Tyco Healthcare Group, LP, Norwalk, Conn.) generally designated as 400 including a handle 402, a barrel 404 extending from the handle 402 and an arm 406 extending from the distal end of the barrel 404. The stapling device 400 further includes an end effector including a staple anvil 408 orthogonally affixed to a distal end of arm 406 and a staple cartridge receiver 410 operatively coupled to the distal end of barrel 404 for holding a disposable staple cartridge 412 thereon.

Turning now to FIGS. 9A and 9B, staple cartridge 412 includes a pair of inclined surfaces 414 projecting outwardly along a central longitudinal axis thereof. Preferably, each of the pair of inclined surfaces 414 is inclined in a direction transverse to the longitudinal axis. Each inclined surface 414 of staple cartridge 412 is provided with a pair of laterally spaced rows of staple retention slots 416. Staple anvil 408 includes a pair of inclined surfaces 418 which project inwardly along a central longitudinal axis thereof and defining a working surface. Preferably, each of the pair of inclined surfaces 418 is inclined in a direction transverse to the longitudinal axis. Each inclined surface 418 of staple anvil 408 is provided with a pair of laterally spaced rows of staple forming depressions 420 formed therein.

Once again, the inclined pair of surfaces 414 projecting from staple cartridge 412 have an angle of inclination which complements an angle of inclination of the pair of inclined surfaces 418 of staple anvil 408. In this manner, when staple anvil 408 is being or is approximated relative to staple cartridge 412, a camming action helps to align staple forming depressions 420 of staple anvil 408 to align with staple retention slots 416 of staple cartridge 412. While the angle of inclination of surfaces 414 of staple cartridge 412 have been shown as projecting outward and the angle of inclination of surfaces 418 of staple anvil 408 have been shown to project inward, it is envisioned that angle of inclination of surfaces 414, 418 can be reversed. While generally planar inclined surfaces have been described, it is envisioned that the inclined surfaces can be replaced with arcuate surfaces in the manner disclosed in FIGS. 4A, 4B and 5 without departing from the breath of the disclosure.

Reference can be made to commonly assigned U.S. Pat. No. 5,964,394 to Robertson, the entire content of which is incorporated herein by reference, for a more detailed explanation of the operation of surgical stapling apparatus 400 and of the approximation of the staple cartridge with the staple anvil.

Figure 12A:
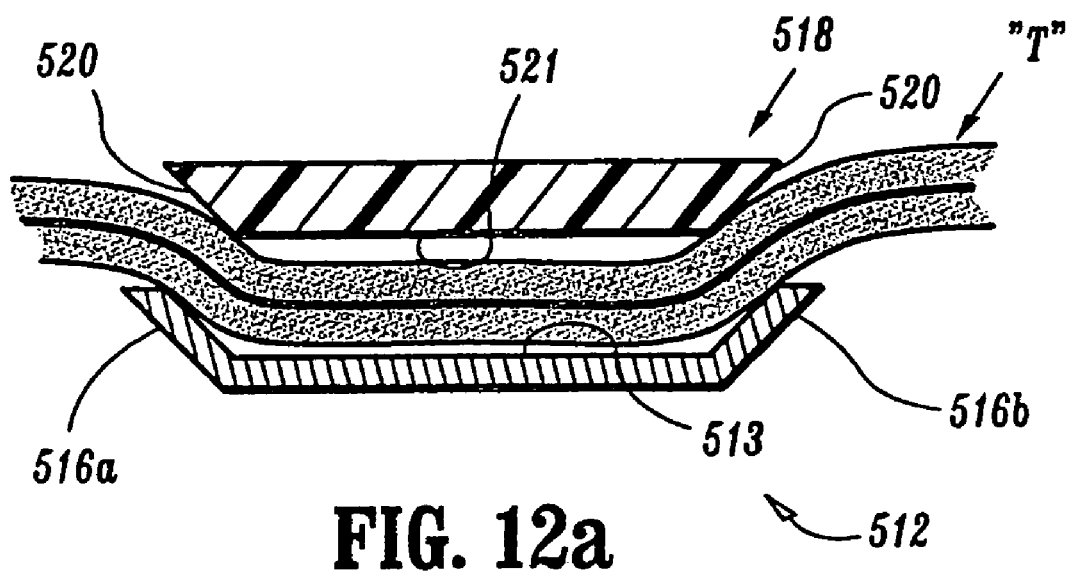
FIG. 12A is a schematic enlarged cross-sectional view of the staple cartridge and staple anvil working surfaces taken along section line 12A-12A of FIG. 11A.

Turning now to FIGS. 10, 11A, 11B, 11C, 12A and 12B, there is shown an alternative surgical stapling apparatus of the end-to-end anastomosis type for performing surgical anastomotic stapling (i.e., an instrument such as an "EEA™" surgical stapling apparatus available from United States Surgical, a division of Tyco Healthcare Group, LP, Norwalk, Conn.), generally depicted as 500. Surgical stapling apparatus 500 includes a handle assembly 502 having at least one pivotable actuating handle member 503, and further includes advancing means 505. Extending from handle assembly 502, there is provided a tubular body portion 504 which may be constructed so as to have a curved shape along its length. Tubular body portion 504 terminates in a staple pusher assembly 506 having a circular staple cartridge 518 including a pair of distally oriented spaced apart annular rows of staple retention slots 519 formed in a distal surface 521 (see FIG. 12A) thereof. As best seen in FIG. 12A, circular staple cartridge 518 preferably includes a pair of annular inclined upstanding side walls 520 which are inclined at an obtuse angle relative to distal surface 521 of staple cartridge 518.

Surgical stapling apparatus 500 further includes a circular anvil assembly 508 having an anvil head 509 and an anvil shaft 510 extending from a proximal end thereof and adapted to engage a trocar shaft 511 extending distally from staple cartridge 518. Anvil head 509 includes an annular anvil 512 disposed at a proximal end thereof, wherein anvil 512 includes a pair of laterally spaced rows of staple deforming depressions 514 (see FIG. 11 IB) formed circumferentially about a surface 513 of anvil 512. Preferably, as best seen in FIG. 12A, anvil 512 further includes a pair of inclined annular upstanding side walls 512, namely, an inner wall 516a and an outer wall 516b, which side walls 516a, 516b are inclined at an obtuse angle relative to surface 513 of anvil 512.

Preferably, the angle of inclination of side walls 516a, 516b of circular anvil 512 complement the angle of inclination of side walls 520 of circular staple cartridge 518. In this manner, when circular anvil 512 is being or is approximated with or relative to circular staple cartridge 518 with tissue "T" therebetween, a camming action takes place between tissue "T" and side walls 516a, 516b and side walls 520 thereby helping to bring staple retention slots 519 into alignment with staple deforming depressions 514. Preferably, side walls 516a, 516b have an angle of inclination which is greater than 90° and less than 180° relative to surface 513 of anvil 512.

While it is shown that circular anvil 512 includes a pair of annular side walls 516a, 516b having an obtuse angle of inclination relative to anvil surface 513 and circular staple cartridge 518 includes a pair of annular side walls 520 having an obtuse angle of inclination relative to surface 521 of staple cartridge 518, it is envisioned that circular anvil 512 may include a pair of annular side walls 516a, 516b having an obtuse angle of inclination relative to surface 513 of anvil 512 while circular staple cartridge 518 includes a pair of inclined upstanding annular side walls 520 having an obtuse angle of inclination relative to distal surface 521 of staple cartridge 518 which complements the angle of inclination of side walls 516a, 516b.

Figure 12B:
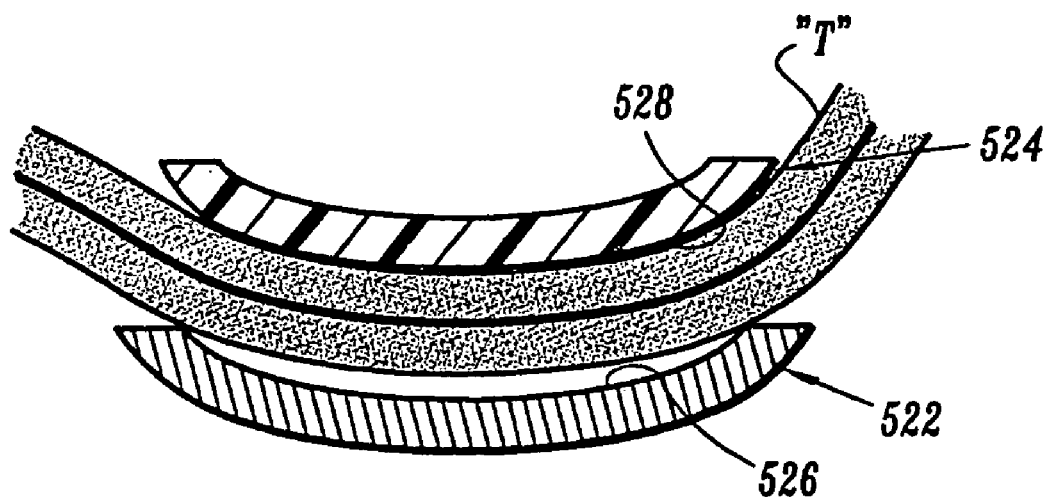
FIG. 12B is a schematic enlarged cross-sectional view of working surfaces of an alternative embodiment of a staple cartridge and staple anvil.

Turning now to FIG. 12B, an alternative cross-section of an anvil surface and a staple cartridge surface are generally shown as 522 and 524, respectively. Anvil surface 522 includes a concave surface 526 for receiving a convex surface 528 of circular staple cartridge 524. Moreover, when arcuate staple cartridge 524 with or is being or is approximated with arcuate anvil surface 522 with tissue "T" therebetween, a camming action takes place between tissue "T" and concave surface 526 of anvil surface 522 and convex surface 528 of staple cartridge surface 524 thereby helping to bring staple retention slots 519 (not shown) of circular staple cartridge 524 into alignment with staple deforming depressions 514 of circular anvil surface 522. Once again, while it is shown that circular staple cartridge 524 includes a concave surface 528 and circular anvil surface 522 includes a convex surface 526, it is envisioned that circular staple cartridge 524 can have the convex surface while the circular anvil can have the concave surface.

Figure 12C:
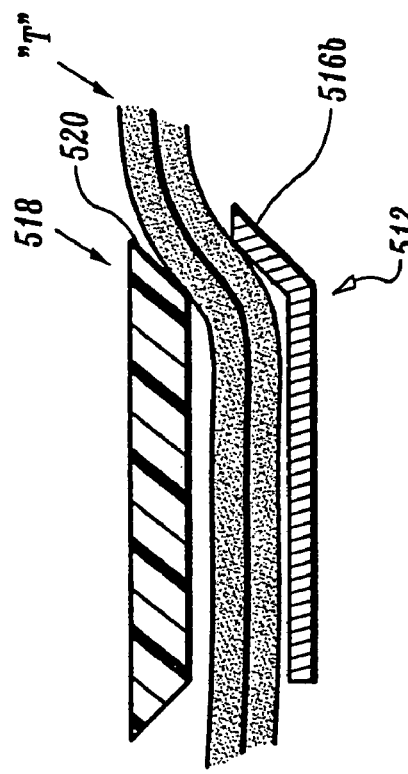
FIG. 12C is a schematic enlarged cross-sectional view of working surfaces of an alternative embodiment of a staple cartridge and staple anvil.
Figure 12D:
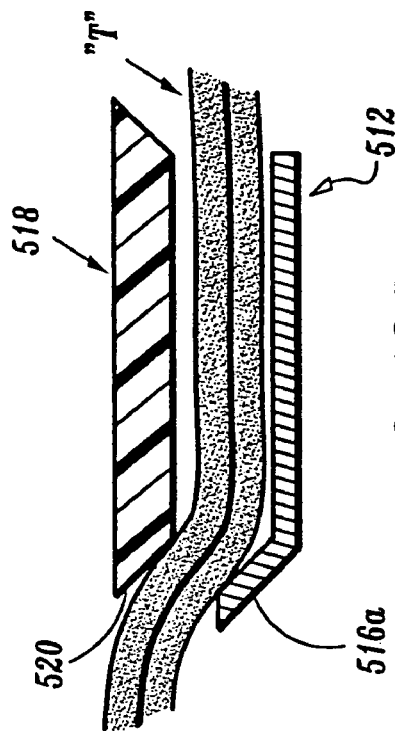
FIG. 12D is a schematic enlarged cross-sectional view of working surfaces of an alternative embodiment of the staple cartridge and staple anvil of FIG. 12C.

As seen in FIGS. 12C and 12D, it is envisioned that anvil 512 is provided either with an inclined inner wall 516a extending from an inner edge thereof (see FIG. 12D) or an inclined outer wall 516b extending from an outer edge thereof (see FIG. 12C). Since inner wall 516a and outer wall 516b are annular, a single inclined wall (i.e., either inner wall 516a or outer wall 516b) is all that is needed in order to properly align staple cartridge 518 with staple anvil 512 upon their approximation to one another. In particular, the camming action between tissue "T" and inner wall 516a or outer wall 516b of anvil 512 with corresponding annular side wall 520 of staple cartridge 518 helps to bring staple deforming depressions 514 into alignment with staple retention slots 519.

It is further envisioned that anvil 512 can include a surface 513 having a pair of inclined surface portions (not shown) terminating in a central ridge (not shown) and a staple cartridge 518 can include a surface 521 having a pair of inclined surface portions (not shown) terminating in a central valley (not shown) (i.e., similar to the configuration of staple cartridge 104 of staple anvil 108).

Figure 12E:
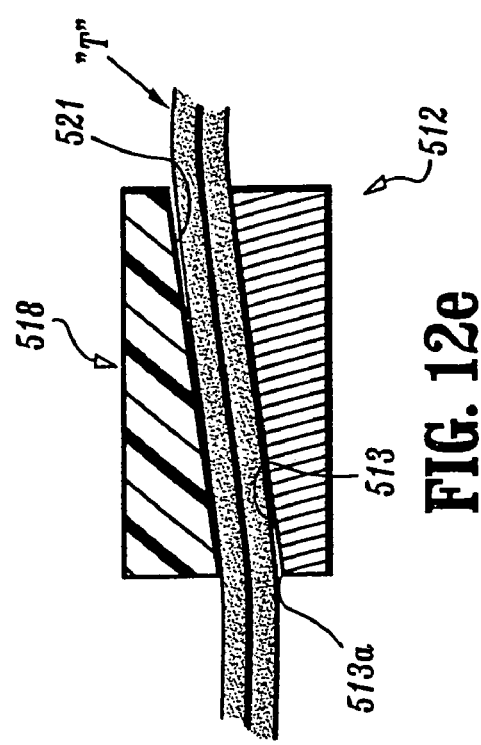
FIG. 12E is a schematic enlarged cross-sectional view of working surfaces of an alternative embodiment of a staple cartridge and staple anvil.
Figure 12F:
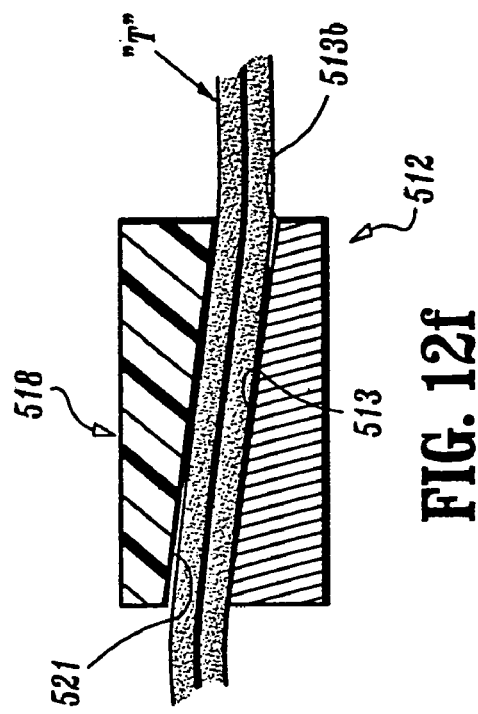
FIG. 12F is a schematic enlarged cross-sectional view of working surfaces of an alternative embodiment of the staple cartridge and staple anvil of FIG. 12E.

In yet another embodiment, as seen in FIGS. 12E and 12F, it is envisioned that anvil 512 is substantially conical and includes a surface 513 which is angled to have an inner edge 513a which is either recessed (see FIG. 12E) or elevated (see FIG. 12F) relative to an outer edge 513b and staple cartridge 518 has a surface 521 which complements the angle of inclination of surface 513 of anvil 512.

It should be appreciated that in each of the above disclosed embodiments, upon approximation of the opposed anvil and cartridge halves of the particular embodiment with tissue "T" therebetween, there is an enhanced opportunity for each of the staple deforming depressions formed in the surface of the anvil to be transversely and longitudinally aligned with a staple retention slot formed in staple cartridge to enhance proper staple formation. The angle at which the staples are oriented relative to the cartridge is determined, e.g., by the formation and disposition of the staple pockets within the cartridge in any given embodiment. In conventional surgical stapling apparatus, for example, the staple pockets are typically oriented to eject the staples perpendicular to the surface of the cartridge. In the embodiments disclosed herein, the staple retention slots may likewise be formed to eject the staples perpendicular to the surface of the staple cartridge or in the case of a curved surface perpendicular to a tangent of the surface of the staple cartridge at the point along the surface where the staple retention slot opening lies. In such curved surface embodiments, the pusher member, which travels longitudinally to cam individual staple pushers contained in the staple retention slots, can have a camming surface which matches the cross-sectional profile of the cartridge surface where the staples are being ejected in order to apply the force necessary to effectively form the staples against the opposed anvil surfaces.

Reference can be made to commonly assigned U.S. Pat. No. 5,915,616 to Viola et al., the entire content of which is incorporated herein by reference, for a more detailed explanation of the operation of surgical stapling apparatus 500 and of mating and/or approximating of a staple cartridge with a staple anvil.

Figure 13:
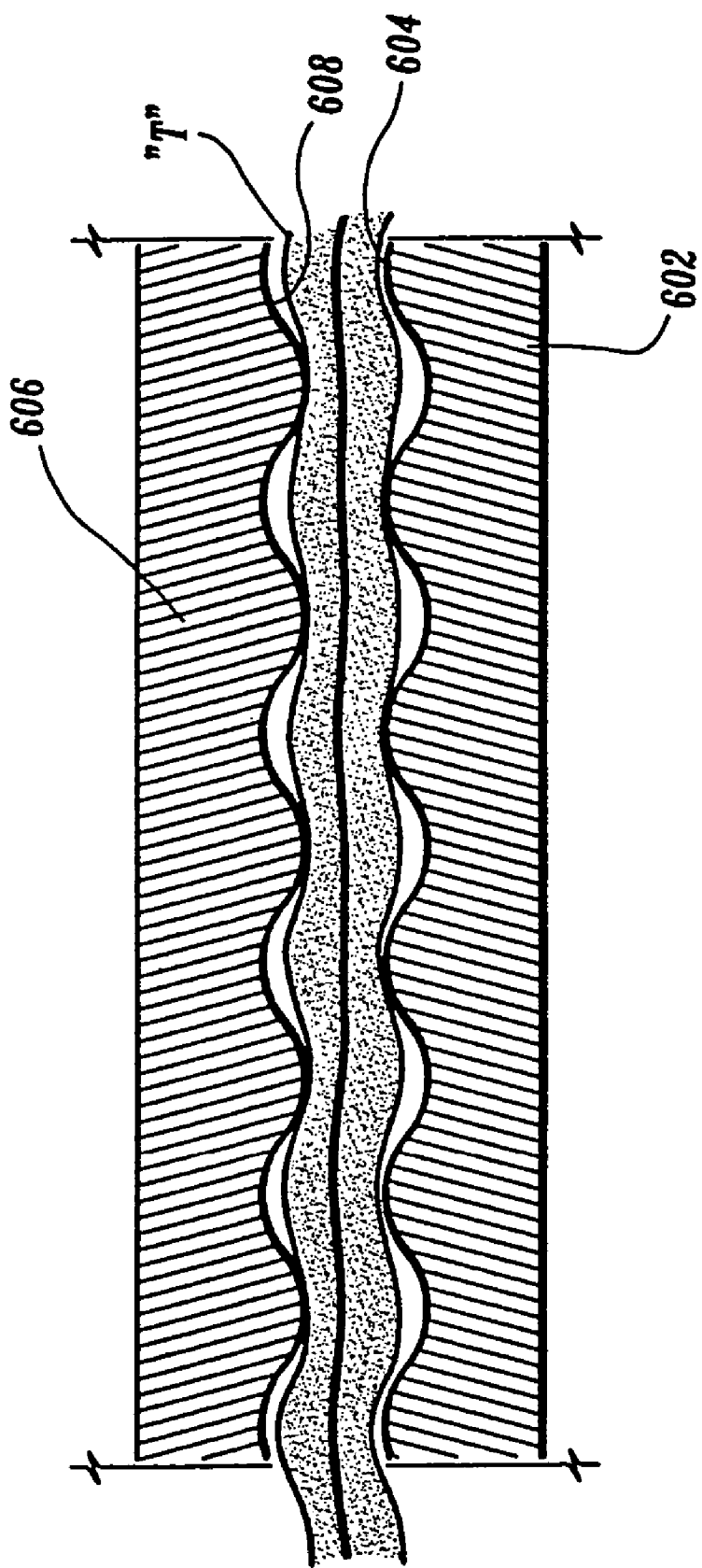
FIG. 13 is a schematic enlarged side elevational view of a portion of working surfaces of a staple cartridge and staple anvil according to a further alternative embodiment of the present disclosure.

Turning now to FIG. 13, an alternative embodiment of a staple cartridge and a staple anvil is shown generally as 602 and 606, respectively. As seen in FIG. 13, staple anvil 602 includes a wave-like or undulating top surface 604 extending longitudinally along the length thereof while staple cartridge 606 includes a wave-like or undulating bottom surface 608 extending longitudinally along a length thereof. Preferably, the cross-sectional profile of undulating top surface 604 complements the cross-sectional profile of juxtaposed undulating bottom surface 608. In this manner, undulating bottom surface 608 and undulating top surface 604 cooperate with one another upon approximation of cartridge 606 with anvil 602 to thereby longitudinally align staple deforming depressions (not shown) formed in anvil 602 with staple retention slots (not shown) formed in cartridge 606. It is envisioned that the transverse alignment configurations described above can be combined with the longitudinal alignment configuration described above in order to help align the staple anvil with the staple cartridge in a longitudinal direction.

It is contemplated that, in an alternate embodiment, that the staple anvil includes a wave-like or undulating topographical surface extending in both a transverse and a longitudinal direction and the staple cartridge include a wave-like or undulating topographical surface, extending in both a transverse and a longitudinal direction, wherein the undulating surface of the staple anvil complements the undulating surface of the staple cartridge. In this manner, when the staple anvil and the staple cartridge are approximated with or relative to one another, the staple deforming depressions and the staple retention slots are substantially transversely and longitudinally aligned with one another.

Figure 14:
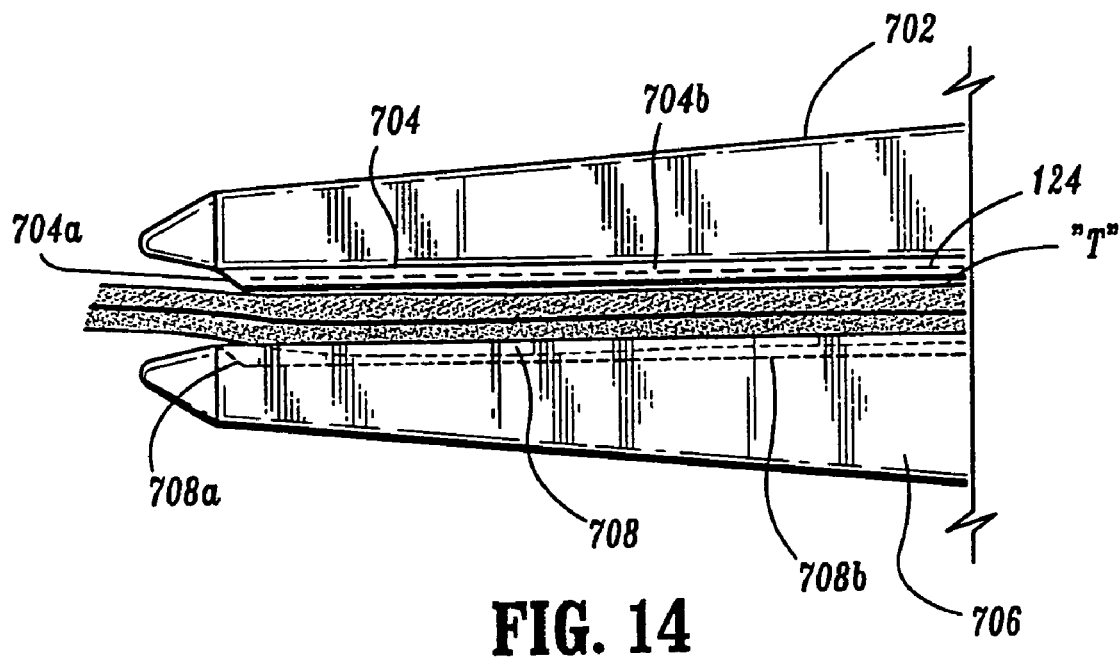
FIG. 14 is a schematic enlarged side elevational view of a portion of an approximated staple cartridge and staple anvil according to yet another alternative embodiment of the present disclosure.
Figure 15:
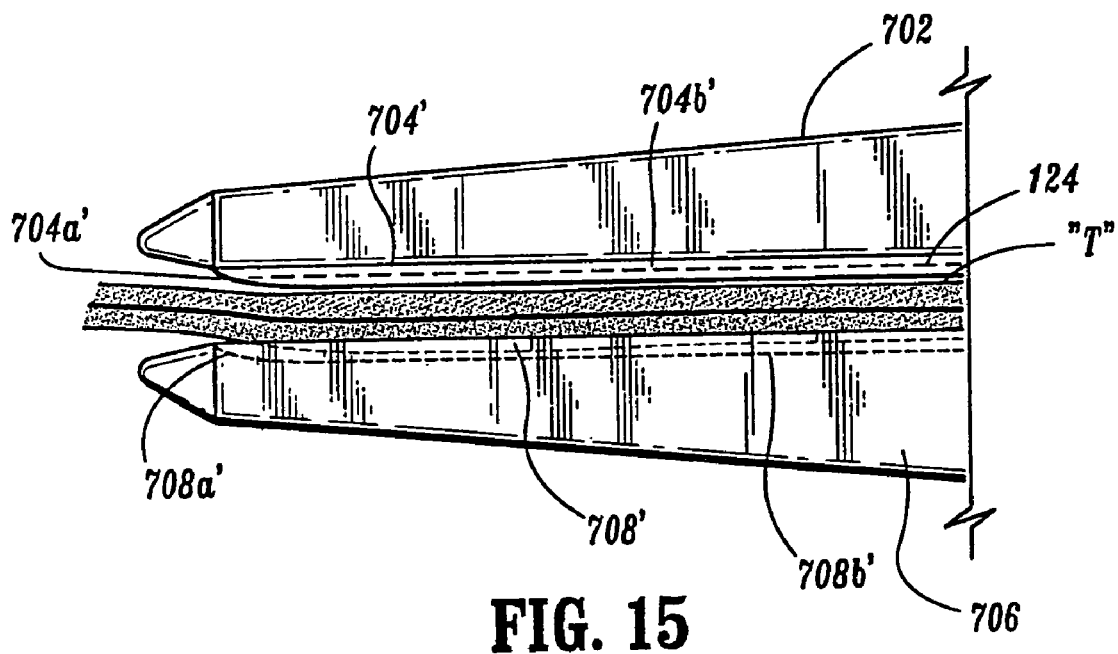
FIG. 15 is a schematic enlarged side elevational view of a portion of an approximated staple cartridge and staple anvil according to still another alternative embodiment of the present disclosure.

Turning now to FIGS. 14 and 15, the distal end portions of a staple anvil and a staple cartridge, in accordance with alternative embodiments of the present disclosure, are shown generally as 702 and 706, respectively.

As seen in FIG. 14, staple cartridge 706 includes a recessed surface 708 formed as part of the tissue contacting surface or working surface of staple cartridge 706. Recessed working surface 708 includes a distal end portion 708a extending at an angle into staple cartridge 706 (e.g., in the form of a ramp) and a more proximal portion 708b extending longitudinally along a length of staple cartridge 706. It is contemplated that proximal portion 708b can have, for example, a V-shaped, rectangular, arcuate, undulating or other suitable cross-sectional profile. Staple anvil 702 includes a projecting working surface 704 extending from the tissue contacting or working surface of staple anvil 702 and in juxtaposition relative to recessed surface 708 of staple cartridge 706. Projecting surface 704 is shaped and sized to complement the size and shape of recessed working surface 708 and preferably includes a distal end portion 704a extending at an angle out of staple anvil 702 (e.g., in the form of a ramp) and a more proximal portion 704b extending longitudinally along a length of staple anvil 702.

As seen in FIG. 15, staple cartridge 706 includes a recessed surface 708' formed in the tissue contacting side of staple cartridge 706. Recessed surface 708' preferably has an elongate concave topographical profile including a concave leading distal end portion 708a' and a more proximal portion 708b' extending longitudinally along a length of staple cartridge 706. Staple anvil 702 includes a projecting surface 704' as or extending from the tissue contacting or working surfaces of staple anvil 702 and in juxtaposition relative to recessed surface 708' of staple cartridge 706. Projecting surface 704' is shaped and sized to complement the size and shape of recessed surface 708' and preferably includes a convex leading distal end portion 704a' extending into a more proximal portion 704b' extending longitudinally along the length of staple anvil 702.

Figure 16:
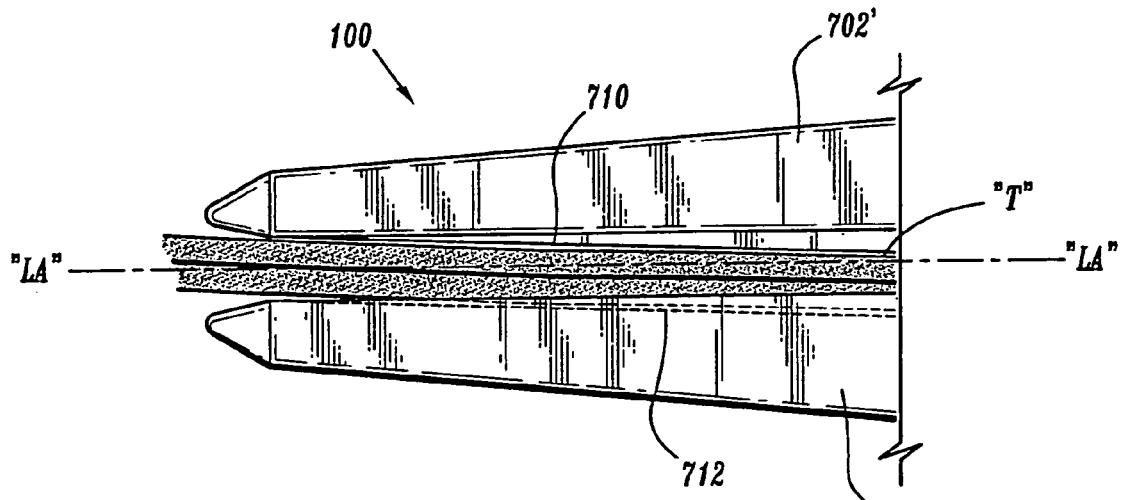
FIGS. 16 and 17 are schematic enlarged side elevational views of portions of the approximated staple cartridge and staple anvil according other alternative embodiments of the present disclosure.
Figure 17:
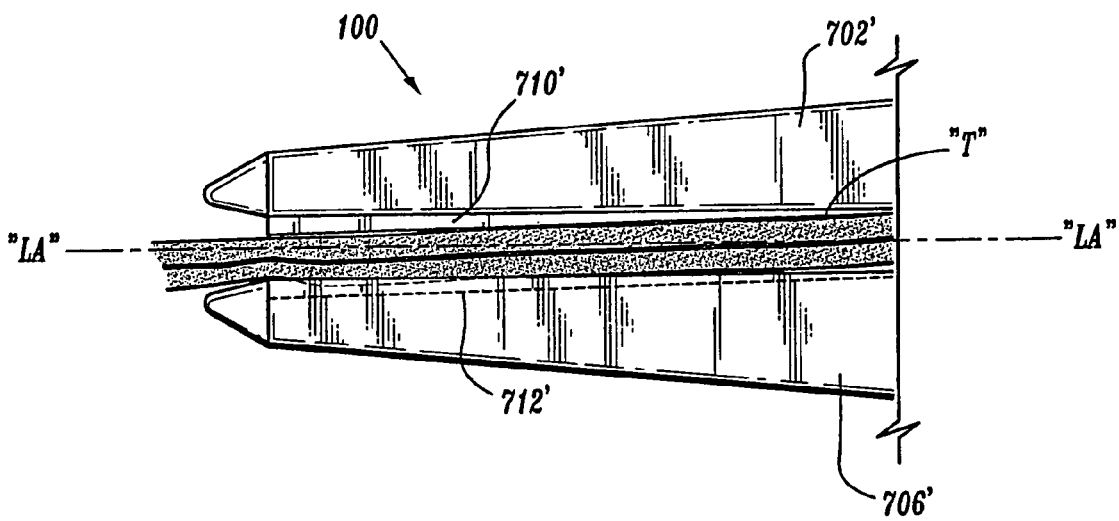

As seen in FIGS. 16 and 17, working surfaces 712 and 710 of staple cartridge 706' and staple anvil 702', respectively, need not be parallel to but can be at an angle relative to the longitudinal axis "LA" of the end effector, the surgical stapling instrument 100 or the respective anvil and/or cartridge. For example, as seen in FIG. 16, the angles of working surfaces 710, 712, of staple cartridge 706' can be generally declining from the distal end or distal end portions of staple cartridge 706' and staple anvil 702', or as shown in FIG. 17, working surfaces 710', 712' can be declining toward the distal end or distal end portions of the respective anvil and cartridge.

It is further contemplated that, in another alternate embodiment, the staple anvil can be provided with a longitudinally running row of detents or dimples formed in the surface of the staple anvil, preferably near at least one longitudinal side edge thereof while the staple cartridge is preferably provided with a longitudinally running row of nubs or projections extending from the surface of the staple cartridge. Accordingly, when the staple anvil is being or is approximated with or relative to the staple cartridge, the nubs of the staple cartridge will force the interstitial tissue into the detents of the staple anvil and such will help to both transversely and longitudinally align the staple deforming depressions with the staple retention slots. It is further envisioned that the nubs of the staple cartridge could be replaced with pins or needles which would penetrate the tissue disposed between the staple anvil and the staple cartridge and then enter the detents or dimples of the staple anvil.

While alignment configurations may extend the entire length and width of the staple anvils and staple cartridges described above, it is envisioned that such alignment features need only be placed or occur at pre-selected locations along a or the length and/or along a or the width, or a portion of the end effector or working surface(s) in order provide a surgical stapling apparatus which helps to align itself upon each mating and/or approximation of the staple anvil with the staple cartridge.

Surgical stapling apparatus disclosed above include a staple anvil or a staple cartridge having a surface with a first shaped topography (i.e., trapezoidal, arcuate, triangular, undulating, etc.) and the other of the staple anvil or staple cartridge having a surface with a second shaped topography which is complementary to the first shaped topography. Accordingly, when the staple cartridge and the staple anvil are being or are approximated with or relative to one another with tissue "T" therebetween, the first shaped topographical surface cooperates with the second shaped topographical surface to help align the staple anvil and the staple cartridge in a transverse and/or longitudinal direction.

By providing a surgical, stapling apparatus including a staple anvil having a shaped working surface together with a staple cartridge having a shaped working surface, which shaped working surfaces complement each other, the staple anvil and the staple cartridge are urged to align with one another each time the staple anvil is brought into approximation with the staple cartridge, thereby also enhancing alignment of staple deforming depressions formed in the staple anvil, with the staple retention slots formed in the staple cartridge. Such configured anvils and cartridges may be suitably formed from suitable materials other than steel which are less expensive and easier to form yet which may achieve the high degree of tolerance for alignment between the staple retention slots and the staple deforming depressions.

Where it is stated herein that there is tissue between a staple cartridge and a staple anvil, it is to be understood that with in lieu of the tissue there could be or also be a suitable surgical material, for a non-limiting example, a Pledget™ material, therebetween.

In accordance with the present disclosure, it is understood that the working surfaces of the surgical staplers disclosed herein can be approximated in any number of methods as are known by those skilled in the art without departing from the scope and/or breath of the present disclosure.

It will be understood that various modifications may be made to the embodiments disclosed herein. Therefore, the above description should not be construed as limiting, but merely as an exemplification of preferred embodiments. Those skilled in the art will envision other modifications within the scope and spirit of the claims appended hereto.

What is claimed is:

1. A surgical stapling apparatus, comprising:
an end effector having a pair of jaws including an anvil and a staple cartridge, the end effector defining a longitudinal axis;
the anvil having a working surface, the working surface of the anvil having a plurality of staple deforming depressions, and the working surface of the anvil defining a first plane intersecting the longitudinal axis to define a first acute angle therebetween; and
the staple cartridge having a plurality of surgical staples and a working surface, the working surface of the staple cartridge having a plurality of staple retention slots, the working surface of the staple cartridge defining a second plane intersecting the longitudinal axis to define a second acute angle therebetween,
wherein the first and second acute angles are defined when the anvil and the staple cartridge are in an approximated position.

2. The surgical stapling apparatus of claim 1, wherein the working surface of the staple cartridge declines from a distal end of the working surface toward a proximal end.

3. The surgical stapling apparatus of claim 1, wherein the working surface of the staple cartridge declines toward a distal end of the working surface.

4. The surgical stapling apparatus of claim 1, wherein the working surface of the anvil corresponds to the working surface of the staple cartridge, 5. The surgical stapling apparatus of claim 1, wherein the working surface of the staple cartridge declines in a direction transverse to the longitudinal axis.

6. The surgical stapling apparatus of claim 5, wherein the pusher member is arranged to apply the force necessary to effectively form the staples against the working surface of the anvil.

7. The surgical stapling apparatus of claim 5, wherein the pusher member has a camming surface which matches the working surface of the staple cartridge where the surgical staples are being ejected.

8. The surgical stapling apparatus of claim 1, wherein the working surface of the anvil declines in a direction transverse to the longitudinal axis.

9. The surgical stapling apparatus of claim 1, further comprising a pusher member disposed in the staple cartridge so as to cam staple pushers to eject the surgical staples from the staple cartridge.

10. The surgical stapling apparatus of claim 1, wherein the first plane is substantially parallel to the second plane.

11. A cartridge for use in a surgical stapling apparatus having a pusher member arranged to cam staple pushers to eject staples from the cartridge, the cartridge comprising:
   an anvil having a plurality of anvil depressions disposed on a working surface;
   a staple cartridge having a plurality of surgical staples and a working surface, the working surface of the staple cartridge having a plurality of staple retention slots, the working surface of the staple cartridge having two planar walls, the planar walls intersecting at a center line of the cartridge, and the planar walls forming an acute angle.

12. The cartridge of claim 11, wherein the working surface of the anvil corresponds to the working surface of the staple cartridge.

13. The cartridge of claim 11, wherein the working surface of the cartridge is inclined along the center line of the cartridge.

14. The cartridge of claim 11, wherein the two walls define a V-shaped cross-sectional profile along the center line.

* * * * *